United States Patent
Chen et al.

(10) Patent No.: US 6,911,573 B2
(45) Date of Patent: Jun. 28, 2005

(54) DUAL-ZONED ABSORBENT WEBS

(75) Inventors: Fung-jou Chen, Appleton, WI (US); Jeffrey Dean Lindsay, Appleton, WI (US); Richard Joseph Kamps, Wrightstown, WI (US); Andrew Michael Lake, Combined Locks, WI (US); Mark Louis Robinson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 524 days.

(21) Appl. No.: 10/042,786

(22) Filed: Jan. 8, 2002

(65) Prior Publication Data

US 2002/0103469 A1 Aug. 1, 2002

Related U.S. Application Data

(60) Division of application No. 09/353,278, filed on Jul. 14, 1999, which is a division of application No. 08/997,287, filed on Dec. 23, 1997, now Pat. No. 5,990,377, which is a continuation-in-part of application No. 08/821,483, filed on Mar. 21, 1997, now abandoned.

(51) Int. Cl.$^7$ ................................................ A61F 13/15

(52) U.S. Cl. .............................. 604/378; 604/385.101; 604/385.01; 156/209; 156/245; 428/131; 162/109

(58) Field of Search ................................ 604/378, 379, 604/385.01, 385.101, 380–382; 428/131–140, 170–172; 156/209, 242, 244.17, 245, 277.2; 162/109, 52

(56) References Cited

U.S. PATENT DOCUMENTS

| 2,391,621 A | 12/1945 | Powell, III et al. |
| 2,576,914 A | 12/1951 | Barrett |

(Continued)

FOREIGN PATENT DOCUMENTS

| EP | 0 353 972 B1 | 1/1994 |
| EP | 0 677 612 B1 | 9/2000 |

(Continued)

OTHER PUBLICATIONS

Derwent World Patent Database abstract of GB 1,593,331: Description of Kemi Oy, "Water Resistant Paper And Board."

(Continued)

*Primary Examiner*—John J. Calvert
*Assistant Examiner*—Jacqueline F. Stephens
(74) *Attorney, Agent, or Firm*—Gregory E. Croft; Patricia A. Charlier

(57) ABSTRACT

The present invention is a method for producing an absorbent article. A wet resillient, cellulosic basesheet having elevated and depressed regions with an Overall Surface Depth of at least 0.2 mm is prepared. The cellulosic basesheet has an upper surface and a lower surface. A contiguous, fibrous nonwoven web having a plurality of openings is integrally attached onto the upper surface of the cellulosic basesheet such that a portion of the openings are superposed over the depressed regions of the cellulosic basesheet. An absorbent core and an impervious web are attached to the lower surface of the cellulosic basesheet such that the absorbent core is sandwiched between the impervious web and the cellulosic basesheet.

15 Claims, 12 Drawing Sheets

U.S. PATENT DOCUMENTS

| | | |
|---|---|---|
| 3,020,178 A | 2/1962 | Sweeney et al. |
| 3,165,485 A | 1/1965 | Ilnyckyj |
| 3,224,926 A | 12/1965 | Bernardin |
| 3,287,149 A | 11/1966 | Dooley et al. |
| 3,339,550 A | 9/1967 | Van Haaften |
| 3,417,040 A | 12/1968 | Kremer |
| 3,455,778 A | 7/1969 | Bernardin |
| 3,485,706 A | 12/1969 | Evans |
| 3,489,148 A | 1/1970 | Duncan et al. |
| 3,494,821 A | 2/1970 | Evans |
| 3,520,542 A | 7/1970 | Crean |
| 3,556,932 A | 1/1971 | Coscia et al. |
| 3,556,933 A | 1/1971 | Williams et al. |
| 3,629,171 A | 12/1971 | Kremer et al. |
| 3,695,269 A | 10/1972 | Malaney |
| 3,700,623 A | 10/1972 | Keim |
| 3,765,997 A | 10/1973 | Dunning |
| 3,772,076 A | 11/1973 | Keim |
| 3,809,089 A | 5/1974 | Hedstrom et al. |
| 3,812,000 A | 5/1974 | Salvucci, Jr. et al. |
| 3,838,692 A | 10/1974 | Levesque |
| 3,881,987 A * | 5/1975 | Benz .................. 162/116 |
| 3,885,158 A | 5/1975 | Flutie et al. |
| 3,899,388 A | 8/1975 | Petrovich et al. |
| 3,929,135 A | 12/1975 | Thompson |
| 3,967,623 A | 7/1976 | Butterworth et al. |
| 3,976,734 A | 8/1976 | Dunning et al. |
| 4,041,951 A | 8/1977 | Sanford |
| 4,100,324 A | 7/1978 | Anderson et al. |
| 4,113,911 A * | 9/1978 | LaFitte et al. |
| 4,117,199 A * | 9/1978 | Gotoh et al. |
| 4,129,528 A * | 12/1978 | Petrovich et al. |
| 4,147,586 A * | 4/1979 | Petrovich et al. |
| 4,208,459 A * | 6/1980 | Becker et al. |
| 4,222,921 A * | 9/1980 | Van Eenam |
| 4,342,314 A * | 8/1982 | Radel et al. |
| 4,391,869 A * | 7/1983 | Cook et al. |
| 4,425,130 A * | 1/1984 | DesMarais |
| 4,445,970 A * | 5/1984 | Post et al. |
| 4,524,474 A * | 6/1985 | Svensson |
| 4,556,450 A * | 12/1985 | Chuang et al. |
| 4,588,457 A * | 5/1986 | Crenshaw et al. |
| 4,610,915 A * | 9/1986 | Crenshaw et al. |
| 4,626,254 A * | 12/1986 | Widlund et al. |
| 4,675,394 A * | 6/1987 | Solarek et al. |
| 4,725,473 A * | 2/1988 | Van Gompel et al. |
| 4,741,941 A * | 5/1988 | Englebert et al. |
| 4,781,710 A | 11/1988 | Megison et al. |
| 4,879,170 A * | 11/1989 | Radwanski et al. |
| 4,929,495 A * | 5/1990 | Stanislawczyk |
| 4,931,355 A * | 6/1990 | Radwanski et al. |
| 4,981,557 A * | 1/1991 | Bjorkquist |
| 5,008,344 A * | 4/1991 | Bjorkquist |
| 5,011,864 A * | 4/1991 | Nielsen et al. |
| 5,048,589 A * | 9/1991 | Cook et al. |
| 5,069,548 A * | 12/1991 | Boehnlein |
| 5,085,736 A | 2/1992 | Bjorkquist |
| 5,156,902 A | 10/1992 | Pieper et al. |
| 5,188,625 A | 2/1993 | Van Iten et al. |
| 5,230,776 A | 7/1993 | Andersson et al. |
| 5,246,545 A | 9/1993 | Ampulski et al. |
| 5,302,382 A | 4/1994 | Kasprzak |
| 5,348,620 A | 9/1994 | Hermans et al. |
| 5,368,910 A | 11/1994 | Langdon |
| 5,389,202 A | 2/1995 | Everhart et al. |
| 5,399,412 A | 3/1995 | Sudall et al. |
| 5,411,636 A | 5/1995 | Hermans et al. |
| 5,423,788 A | 6/1995 | Rollins et al. |
| 5,429,686 A | 7/1995 | Chiu et al. |
| 5,431,643 A | 7/1995 | Ouellette et al. |
| 5,437,653 A | 8/1995 | Gilman et al. |
| 5,454,801 A | 10/1995 | Lauritzen |
| 5,478,335 A | 12/1995 | Colbert |
| 5,491,190 A | 2/1996 | Sandvick et al. |
| 5,492,598 A | 2/1996 | Hermans et al. |
| 5,501,768 A | 3/1996 | Hermans et al. |
| 5,516,572 A | 5/1996 | Roe |
| 5,536,555 A | 7/1996 | Zelazoski et al. |
| 5,552,020 A | 9/1996 | Smith et al. |
| 5,562,645 A | 10/1996 | Tanzer et al. |
| 5,591,306 A | 1/1997 | Kaun |
| 5,591,309 A | 1/1997 | Rugowski et al. |
| 5,598,643 A | 2/1997 | Chuang et al. |
| 5,601,871 A | 2/1997 | Krzysik |
| 5,635,191 A | 6/1997 | Roe et al. |
| 5,653,930 A | 8/1997 | Noda et al. |
| 5,667,636 A | 9/1997 | Engel et al. |
| 5,670,110 A | 9/1997 | Dirk et al. |
| 5,763,044 A * | 6/1998 | Ahr et al. .................. 428/131 |
| 5,779,860 A | 7/1998 | Hollenberg et al. |
| 5,840,403 A | 11/1998 | Trokhan et al. |
| 5,990,377 A | 11/1999 | Chen et al. |
| 6,242,074 B1 * | 6/2001 | Thomas .................. 428/137 |
| 2002/0099347 A1 | 7/2002 | Chen et al. |
| 2002/0103469 A1 | 8/2002 | Chen et al. |

FOREIGN PATENT DOCUMENTS

| | | |
|---|---|---|
| JP | 3-185 197 A | 8/1991 |
| WO | WO 95/13773 A1 | 5/1995 |
| WO | WO 95/13774 A1 | 5/1995 |
| WO | WO 97/18784 A1 | 5/1997 |
| WO | WO 97/48854 A1 | 12/1997 |

OTHER PUBLICATIONS

AATCC Test Method 66–1990, Technical Manual of the American Association of Textile Chemists and Colorists, 1995, pp. 99–100.

Adams, Kurt L., Bernard Miller, and Ludwig Rebenfeld, "Forced In–Plane Flow of an Epoxy Resin in Fibrous Networks," *Polymer Engineering And Science*, Mid–Nov., 1986, vol. 26, No. 20, pp. 1434–1441.

Back, Ernst L., "The Pore Anisotrophy of Paper Products and Fibre Building Boards," *Svensk Papperstidning arg. 69*, Nr. 7, Apr. 15, 1966, pp. 219–224.

Bear, Jacob, "Dynamics of Fluids in Porus Media," American Elsevier, New York, NY, 1972, pp. 136–151.

Bieman, Leonard H., Kevin G. Harding, and Albert Boehnlein, "Absolute Measurement Using Field Shifted Moir´´," *SPIE Optical Conference Proceedings*, Nov. 1991, vol. 1614, pp. 259–264.

Bowden, Edward V., "Non–Contact Drying and Turning— the 'On Machine' Technology of the Nineties," *Appita*, vol. 44, No. 1, Jan. 1991, pp. 41–46.

Cadeyes Product Guide, Medar, Inc., Farmington Hills, MI, 1994, pp. 1–19.

Dullien, F. A. L., "Porous Media: Fluid Transport and Pore Structure," Academic Press, New York, 1979, pp. 78–83.

Horstmann, Diane H., Jeffrey D. Lindsay, and Robert A. Stratton, "Using Edge–Flow Tests to Examine the In–Plane Anisotropic Permeability of Paper," *Tappi Journal*, 74(4), Apr. 1991, pp. 241–247.

Lindsay, Jeffrey D. and Jill R. Walin, "Characterization of In–Plane Fluid Flow in Paper," *AIChE Proceedings 1989 and 1990 Forest Products Symposium*, Tappi Press, Atlanta, GA, 1992, pp. 121–129.

Lindsay, Jeffrey D., "Displacement Dewatering To Maintain Bulk," *Paperi Ja Puu—Paper And Timber*, vol. 74, No. 3, 1992, pp. 232–242.

Lindsay, Jeffrey D. and Paul H. Brady, "Studies of Anisotropic Permeability With Applications to Water Removal in Fibrous Webs: Part 1," *Tappi Journal*, vol. 76, No. 9, Sep. 1993, pp. 119–125.

Lindsay, Jeffrey D. and Paul H. Brady,"Studies of Anisotropic Permeability With Applications to Water Removal in Fibrous Webs: Part 2," *Tappi Journal*, vol. 76, No. 11, Nov. 1993, pp. 167–174.

Lindsay, Jeffrey D., "Relative Flow Porosity in Fibrous Media: Measurements and Analysis, Including Dispersion Effects," *Tappi Journal*, vol. 77, No. 6, Jun. 1994, pp. 225–239.

Mummery, Leigh, "Surface Texture Analysis: The Handbook," Hommelwerke GmbH, Muhlhausen, Germany, 1990, pp. 28–29.

* cited by examiner

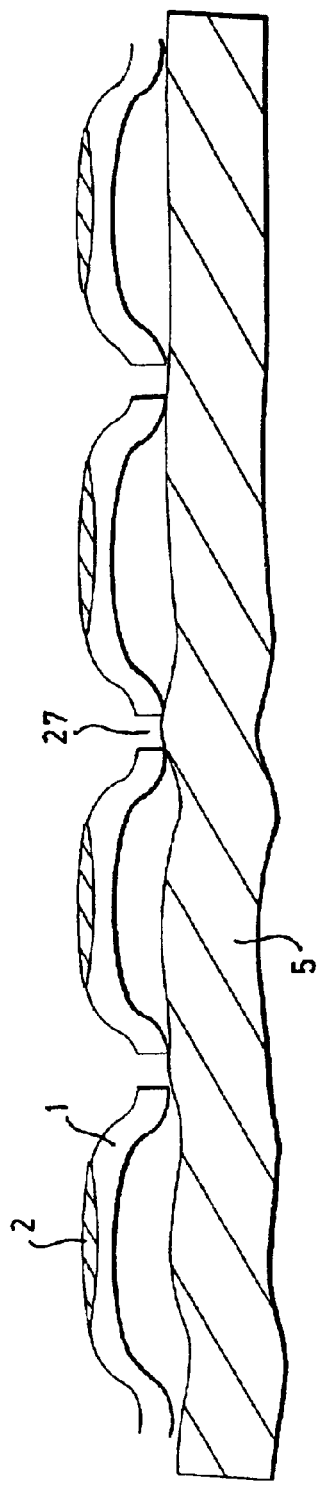
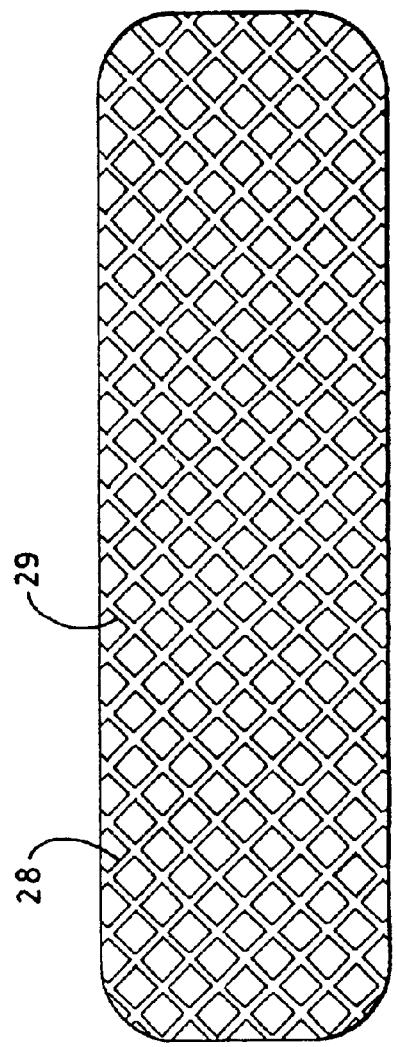

| Properties of Examples 3-6 | Example 3 | Example 4 | Example 5 | Example 6 |
|---|---|---|---|---|
| Furnish | NSWK | NSWK | Spruce BCTMP | Spruce BCTMP |
| Kymene | 0 | 20#/ton | 0 | 20#/ton |
| Basis weight, gsm | 31.7 | 32.2 | 32.4 | 32.7 |
| MD grams dry | 1592 | 2761 | 1678 | 2257 |
| MD % stretch dry | 7.6 | 10.0 | 1.8 | 1.8 |
| CD grams dry | 1671 | 2459 | 1540 | 1872 |
| CD % stretch dry | 5.0 | 5.7 | 3.5 | 3.2 |
| GMT grams dry | 1631 | 2606 | 1608 | 2056 |
| MD grams wet | 106 | 892 | 49 | 826 |
| MD % stretch wet | 13.4 | 8.8 | 6.8 | 3.2 |
| CD grams wet | 71 | 715 | 47 | 759 |
| CD % stretch wet | 9.0 | 5.3 | 5.5 | 3.2 |
| GMT grams wet | 87 | 798 | 48 | 792 |
| MD % wet/dry | 6.6 | 32.3 | 2.9 | 36.6 |
| CD % wet/dry | 4.2 | 29.1 | 3.1 | 40.5 |
| GMT % wet/dry | 5.3 | 30.6 | 3.0 | 38.5 |
| 1-Sheet TMI mm | .602 | .605 | .630 | .602 |
| 10-Sheet TMI mm | 3.34 | 3.68 | 3.91 | 3.95 |
| Density, g/cc | .053 | .053 | .051 | .054 |
| Bulk cc/g | 19.0 | 18.8 | 19.4 | 18.4 |
| Horizontal Absorb. at 0.075 psi, g/g | 7.6 | 8.7 | 10.2 | 10.1 |
| Tilted Absorbency at 0.075 psi, g/g | 7.1 | 7.6 | 9.7 | 9.3 |
| Percent Wet Wrinkle Recovery | 34.4 | 52.7 | 35.0 | 81.6 |
| Springback | .46 | .73 | .66 | .85 |
| WCB, cc/g | 5.2 | 6 | 7.1 | 7.9 |
| LER | .49 | .65 | .65 | .83 |

FIG. 16

|  | Example 7 | Example 8 | Example 9 | Example 10 |
|---|---|---|---|---|
| Basis weight, gsm | 13.6 | 17.6 | 23.9 | 30.1 |
| MD grams dry | 1167 | 649 | 1091 | 1605 |
| MD % stretch dry | 1.4 | 3.7 | 4.0 | 5.1 |
| CD grams dry | 630 | 727 | 1130 | 1624 |
| CD % stretch dry | 2.6 | 3.5 | 4.0 | 4.0 |
| GMT grams dry | 857 | 687 | 1110 | 1614 |
| MD grams wet | 393 | 294 | 465 | 671 |
| MD % stretch wet | 1.5 | 5.0 | 5.5 | 5.5 |
| CD grams wet | 223 | 251 | 429 | 586 |
| CD % stretch wet | 2.4 | 3.3 | 3.5 | 3.5 |
| GMT grams wet | 296 | 272 | 447 | 627 |
| MD % wet/dry | 33.7 | 45.3 | 42.6 | 41.8 |
| CD % wet/dry | 35.4 | 34.5 | 38.0 | 36.1 |
| GMT % wet/dry | 34.5 | 40.0 | 40.3 | 38.8 |
| 1-Sheet TMI mm | .335 | .533 | .610 | .655 |
| 10-Sheet TMI mm | 1.94 | 2.91 | 4.00 | 4.55 |
| Bulk cc/g | 24.6 | 30.3 | 25.5 | 21.8 |
| Horizontal Absorb. at 0.075 psi, g/g | 12.2 | 13.3 | 13.0 | 11.8 |
| Tilted Absorbency at 0.075 psi, g/g | 11.4 | 11.8 | 11.3 | 10.2 |
| Density, g/cc | .041 | .033 | .039 | .046 |
| Percent Wet Wrinkle Recovery | 73.8 | 76.7 | 85.0 | 86.7 |
| Springback | NA | .791 | .841 | .838 |
| WCB, cc/g | NA | 8.2 | 8.1 | 8.0 |
| LER | NA | .802 | .783 | .808 |

FIG. 17

DUAL-ZONED ABSORBENT WEBS

This application is a divisional application of application Ser. No. 09/353,278 entitled "DUAL-ZONED ABSORBENT WEBS" filed in the U.S. Patent and Trademark Office on Jul. 14, 1999, which application is a divisional application of application Ser. No. 08/997,287 entitled "DUAL-ZONED ABSORBENT WEBS" filed in the U.S. Patent and Trademark Office on Dec. 23, 1997, now U.S. Pat. No. 5,990,377 which application is a continuation-in-part of application Ser. No. 08/821,483 entitled "DUAL-ZONED ABSORBENT WEBS" filed in the U.S. Patent and Trademark Office on Mar. 21, 1997 now abandoned. The entirety of application Ser. No. 09/353,278 is hereby incorporated by reference.

BACKGROUND OF THE INVENTION

Absorbent articles are typically used in contact with skin. Some absorbent articles such as disposable diapers, feminine pads, panty liners, incontinence pads and the like are held in contact with skin to absorb body liquids or exudates, while other absorbent materials such as paper towels, hand towels, and wipers may be held in the hands to absorb liquid on the skin or other surfaces. In virtually every case, it is desired that the absorbent article or material keep liquids off the skin to provide a clean, dry feel and to reduce skin health problems that arise from excess hydration or from contact with harmful biological or chemical materials in the liquid being absorbed.

While paper towels and wipers are often composed of a homogenous material, such as an entirely cellulosic web, absorbent articles intended to absorb body fluids typically have at least three layers of different materials. Next to the user's skin is a topsheet layer, sometimes herein referred to as a liner, body-side liner or cover sheet. Beneath the topsheet is the absorbent core that is designed to retain liquid, and beneath the absorbent core is a fluid-impervious backsheet that prevents leakage and maintains the integrity of the product. The topsheet should feel soft and should have high liquid permeability to allow body fluid such as urine, menses, or runny bowel movement to be absorbed and transported away from the skin to reach the central absorbent core. Ideally, the topsheet provides a "dry touch" or "dry feel" by preventing liquid from flowing back to the skin. It is also desirable that the topsheets have high wet resiliency to maintain their bulk and shape when wet.

Traditional hydrophilic cover materials or topsheets in contact with the skin can serve effectively to transport body fluids into the absorbent core, but they cause a wet feel against the skin of the user and may adversely affect skin health. Further, they may wick liquid in the plane of the layer, allowing liquid to approach the edges of the absorbent article and possibly leak or seep out.

To achieve the goal of softness and a dry feel in topsheets of absorbent articles, many manufacturers have turned to nonwoven fabrics made of hydrophobic fibers for the body-contacting topsheet. While the use of hydrophobic nonwoven fabrics may have resulted in improved dry feel, the hydrophobic material hinders wicking into the absorbent core, offers little absorbent capacity and reduces liquid permeability. Further, the poor absorbency of most hydrophobic materials causes any liquid retained therein to be easily squeezed out by body motion of the wearer.

Others have sought to improve the poor wicking and absorbent properties of hydrophobic materials by applying a finish comprising surfactants on the surface of the hydrophobic fibers. This approach may offer some benefits when the article is first wetted, but the surfactants tend to be washed away, resulting in poorer performance upon further wetting.

In the case of absorbent pads for feminine care, two distinct approaches involving hydrophobic topsheets or covers are common. One approach is to use a soft, clothlike nonwoven hydrophobic material, which increases comfort but has the drawback of poor intake of menses. Another approach is to use an apertured plastic film of hydrophobic polymer or other materials. The hydrophobic cover material repels many body fluids, while the apertures allow wicking away from the cover into the absorbent material beneath.

In theory, the hydrophobic apertured material should allow the user's skin to remain relatively dry while allowing wicking in the z-direction (normal to the plane of the cover) into the underlying absorbent core. In practice, hydrophobic apertured films present a number of problems. Apertured films have the drawback of being disliked by some users for their plastic feel and for their poor absorbency. Their hydrophobic nature resists transport through the material, possibly delaying wicking into the absorbent core. Likewise, pockets or pools of liquid may form between the film and the user's skin. In the absence of hydraulic pressure or physical compression, menses in particular may pool on the hydrophobic surface and not penetrate into the apertures, especially if there is a significant interfacial gap between the cover and the underlying absorbent material.

Therefore there is a need for an improved topsheet material which provides the clean feel said to be characteristic of hydrophobic topsheet materials, while also providing for rapid z-direction (depthwise) transport of liquid through the topsheet into the underlying absorbent core, a characteristic more typical of hydrophilic materials. Preferably, these absorbent topsheets also have wet resiliency and absorbency properties which persist upon multiple insults of urine or other liquids.

SUMMARY OF THE INVENTION

The present invention pertains to composite, resilient materials that offer the once-thought mutually exclusive benefits of high absorbency and a clean, dry feel when used as skin-contacting layers that absorb body fluids or other liquids.

In copending U.S. application Ser. No. 08/614,420, "Wet Resilient Webs and Disposable Articles Made Therewith," by F.-J. Chen et al., herein incorporated by reference, a novel wet-laid tissue web is taught having unusually high bulk, wet resiliency, in-plane permeability, and absorbency. The unusual properties of this material are achieved through a combination of high yield fibers, wet strength additives, and noncompressive drying of a molded, three-dimensional structure. The three-dimensional structure of this material does not collapse readily when wetted and thus reduces the contact area with the skin when wet, contributing to a relatively dry feel. It has been found that the inherently hydrophilic material of this previous invention and related materials can be made substantially more useful in personal care articles by the selective addition of hydrophobic material which can impart increased dry feel and, in some embodiments, improved softness. With hydrophobic material deposited on the uppermost, body-contacting regions of the three-dimensional hydrophilic web, the highest body-contacting regions are made substantially hydrophobic to increase the sensation of a clean, dry feel, while a plurality of hydrophilic regions in said web remain accessible to body fluids, allowing liquids to be wicked away from the body and into an absorbent medium. Thus, dry feel and high absorbency are achieved in a single unitary layer or in a single composite structure which may be a laminate of hydrophobic and hydrophilic materials. The hydrophobic material is bonded or integrally attached to the basesheet. Improved disposable absorbent articles comprising such materials include feminine pads and panty liners, incontinence products such as diapers and liners, bed pads, disposable diapers, pull-ups or disposable training pants, disposable menstrual pants, poultry pads, disposable sweat bands or pads, breast pads, odor absorbing pads for shoes, towels, moisturized wipes, wipers, medical pads, bandages and sterile pads for wounds, disposable garments, liners for helmets or other protective or athletic gear, pads for use in waxing automobiles and other surfaces, and so forth. A simple example of an absorbent article containing a topsheet, absorbent core and a backsheet is illustrated in U.S. Pat. No. 3,809,089 issued May 7, 1974 to Hedstrom et al., which is hereby incorporated by reference.

In general, it has been discovered that the addition of hydrophobic agents or materials on relatively elevated portions of one surface of a three-dimensional, wet resilient fibrous web, said web predominantly comprising intrinsically hydrophilic fibers, can enhance the suitability of such webs for use in absorbent articles by reducing the amount of fluid that can remain in contact with the skin or flow back to the skin during use as an absorbent article, thus resulting in an improved dry feel. Certain hydrophobic materials such as short, fine synthetic fibers can provide a pleasant soft, fuzzy, and dry feel, while others such as hydrophobic resins, gels, emulsions, waxes, or liquids can increase the apparent smoothness or lubricity of the surface and improve the tactile properties.

Suitable basesheets can be prepared from aqueous slurries of papermaking fibers with known papermaking techniques. The fibers may be derived from wood or other sources of cellulose and preferably containing a portion of high yield or other wet resilient pulp fibers and an effective amount of wet strength agents. The basesheet can be textured by through-drying on a three-dimensional fabric or other means known in the art and preferably non-compressively dried to give a three-dimensional structure. The inherent stiffness of wet resilient pulp fibers may be reduced, if desired, by incorporation of a suitable plasticizer such as glycerol or by mechanical treatment such as microstraining, dry creping, or calendering.

Through-drying fabrics well suited for formation of three-dimensional webs are disclosed in U.S. Pat. No. 5,429,686, issued to Chiu et al., "Apparatus for Making Soft Tissue Products," issued Jul. 4, 1995, herein incorporated by reference. Other methods such as wet molding, forming on three-dimensional forming fabrics, drying on nonwoven substrates, rush transfer onto embossing fabrics, embossing, stamping, and so forth may be used to create useful three-dimensional structures. The basesheet may be formed as a unitary multilayer structure in which various plies are well bonded and intimately connected to each other. Unitary multilayer basesheets may be formed using layered or stratified headboxes in which two or more furnishes are provided into separate chambers of a headbox, or they may be formed using separate headboxes by couching the wet webs together prior to drying in order to allow extensive hydrogen bonding to develop between the plies during drying, or they may be formed during air-laying by varying the composition of the fibers and additives imparted to web. Multilayer sheets allow better control of physical properties by tailoring the material composition of each layer. For example, a unitary multilayer basesheet us ful for the present invention would have an upper layer, corresponding to the upper surface of the basesheet, and at least one remaining layer below said upper layer and integrally attached thereto, preferably through hydrogen bonds formed between cellulosic fibers during drying, wherein said upper layer differs from at least one remaining layer of the basesheet in terms of material composition. The difference in material composition may be due to differences in fiber species (for example, percentage of hardwood versus softwood); fiber length; fiber yield; fiber treatment with processes which change fiber morphology or chemistry such as mechanical refining, fiber fractionation, dispersing to impart curl, steam explosion, enzymatic treatment, chemical crosslinking, ozonation, bleaching, lumen loading with fillers or other chemical agents, supercritical fluid treatment, including supercritical fluid extraction of agents in the fiber or supercritical fluid deposition of solutes on and into the cell wall, and the like. The difference in material composition between the upper layer and at least one other layer in the basesheet also may be due to differences in added chemicals, including the type, nature, or dosage of added chemicals. The chemicals added differentially to at least one layer of the web may include debonding agents, anti-bacterial agents, wet strength resins, starches, proteins, superabsorbent particles, fiber plasticizers such as glycols, colorants, opacifiers, surfactants, zinc oxide, baking soda, silicone compounds, zeolites, activated carbon, and the like. In a preferred embodiment, the basesheet structure has a wet resilient, noncompressively dried lower layer, preferably composed of softwood fibers, preferably including at least 10% of high yield fiber such as spruce BCTMP, and a soft upper layer containing a portion of finer fibers such as chemically pulped hardwoods. The multilayer basesheet structure is unitary, meaning that the two layers are intimately connected or bonded together. For example, a two-layer unitary basesheet could be formed with a layered headbox or by couching together two wet sheets prior to drying to form intimate contact and hydrogen bonding between the two layers.

The portion of the surface area treated with hydrophobic materials should be great enough to provide an effective improvement in comfort, which will in part depend on the specific product . Accordingly, the fraction of the basesheet surface covered by hydrophobic material can be about 5% or greater, more specifically about 10% or greater, more specifically about 20% or greater, more specifically about 30% or greater, and still more specifically from about 40% to about 75%. The portion of the surface area of the basesheet that remains essentially hydrophilic can be about 10% or greater, more specifically about 20% or greater, more specifically about 30% or greater, more specifically about 40% or greater, more specifically from about 20% to about 90%, and still more specifically from about 50% to about 90%. For effective fluid removal, the lateral width of the depressed hydrophilic regions should be about 0.1 mm or greater, more specifically about 0.5 mm or greater, and still more specifically about 1 mm or greater. The spacing between depressed hydrophilic regions can be about 0.4 mm or greater, more specifically about 0.8 mm or greater, and still more specifically about 1.5 mm or greater. The minimum width of the elevated regions can be about 0.5 mm or greater, more specifically about 1 mm or greater, and still more specifically from about 1 to about 3 mm.

In one preferred embodiment, the hydrophobic matter comprises a substantially contiguous network of hydrophobic fibers having a plurality of macroscopic openings such that a portion of the depressed regions of the basesheet are aligned with openings in the overlaying network of hydrophobic fibers to allow body exudates to pass through the macroscopic openings into the basesheet. A macroscopic opening is defined as an opening that is large relative to the intrinsic pore size of the material. In a typical spunbond or bonded carded web, for example, a macroscopic opening would appear to the eye to be a deliberately introduced hole or void in the web rather than a characteristic pore between adjacent fibers, and specifically could have a characteristic width of about 0.2 mm or greater, about 0.5 mm or greater, about 1 mm or greater, about 2 mm or greater, about 4 mm or greater, about 6 mm or greater, or from about 1 mm to about 5 mm. The characteristic width is defined as 4 times the area of the aperture divided by the perimeter.

The nonwoven web may be made from synthetic fibers, as is known in the art, and may be a spunbond web, a meltblown web, a bonded carded web, or other fibrous nonwoven structures known in the art. For example, a polyolefin nonwoven web such as a low basis weight spunbond material could be provided with apertures through pin aperturing; perf embossing and mechanical stretching of the web; die punching or stamping to provide apertures or holes in the web; hydroentangling to impart apertures by a rearrangement of the fibers due to the interaction of water jets with the fibrous web as it resides on a patterned, textured or three-dimensional substrate that imparts a pattern to the web; water knives that cut out desired apertures or holes in the web; laser cutters that cut out portions of the web; patterned forming techniques, such as air laying of synthetic fibers on a patterned substrate to impart macroscopic openings; needle punching with sets of barbed needles to engage and displace fibers; and other methods known in the art. Preferably, the openings are provided in a regular pattern over at least a portion of the topsheet of the absorbent article.

Preferably, the openings in the network of hydrophobic fibers are spaced and registered with respect to the structure of the basesheet such that a predetermined fraction of the openings are largely superposed over depressed regions of the basesheet. An opening is said to be largely superposed over a depressed region if at least half of the area of the macroscopic opening resides over a depressed region of the basesheet. The predetermined fraction of the openings that are largely superposed over depressed regions can be about 0.25 of greater, 0.4 or greater, 0.5 or greater, 0.7 or greater, 0.8 or greater, or from about 0.4 to about 0.85. The contiguous network of hydrophobic matter is laminated to or otherwise physically joined with the underlying basesheet. Preferably, the network of hydrophobic fibers is attached to the basesheet by means of adhesives and related agents, including hot melts, latexes, glues, starch, waxes, and the like, which adhere or join the upper regions of the basesheet with adjacent portions of the overlaying network of hydrophobic fibers. Preferably, adhesives are applied only to the most elevated portions of the basesheet to effect the bonding between the hydrophilic basesheet and the network of hydrophobic fibers with macroscopic openings therein, leaving the depressed regions substantially free of adhesives. Adhesive application can be through meltblown application of hot melt glues and thermoplastic materials, spray or swirl nozzles of melted or dissolved adhesives, printing of adhesive material onto one or both surfaces before joining, and the like. If adhesives are applied directly to the basesheet by means of spray, mist, aerosol, or droplets in any form, prior to contact of the basesheet with the hydrophobic matter, then it is desirable to use a template or patterned shield to prevent application of adhesive to the depressed regions of the basesheet and to ensure that adhesives are preferentially applied to the elevated portions of the basesheet.

For improved comfort, the network of hydrophobic fibers use in the above-mentioned embodiment preferably is one that is perceived as soft and conformable when next to the skin.

For optimum efficiency in the embodiment comprising a nonwoven web, the apertures or openings in the web should be arrayed in a pattern corresponding to the array of depressed regions in the tissue basesheet, or should correspond to a subset of the depressed regions of the basesheet. Applicant have found a useful means for providing apertures in a nonwoven web in a pattern which corresponds geometrically to the depressed regions of a molded, three-dimensional basesheet wherein the basesheet was molded on a foraminous textured substrate such as a three-dimensional through-drying fabric. The method involves hydroentrangling, which is a well known principle involving the use of high pressure water jets to modify a fibrous surface. Basic principles of hydroentangling are disclosed by Evans in U.S. Pat. No. 3,485,706 issued in 1969, and in U.S. Pat. No. 3,494,821 issued in 1970, both of which are herein incorporated by reference. Hydroentangling, as is known in the art, can be used to impart apertures to a nonwoven web. In one well known technique, the nonwoven web is carried on a textured, permeable carrier fabric. The action of water jets on the nonwoven web as it resides on the textured fabric causes fibers to be moved away from the elevated portions of the carrier fabric on which the nonwoven web reside, resulting in apertures where the carrier fabric was elevated. If a nonwoven web is placed on the same kind of throughdrying fabric that was used to mold a three-dimensional through-dried sheet, preferably an uncreped or only lightly creped sheet in order to preserve texture in the basesheet, then the high places on the carrier TAD fabric will become apertured regions in the nonwoven basesheet. The high portions of the TAD fabric will correspond to the depressed regions on the fabric side of the through-dried sheet. Alternatively, if the nonwoven web is hydroentangled against the backside of a three-dimensional TAD fabric, the elevated regions of the TAD fabric's backside will generally correspond to the depressed in the air side of the sheet that is through dried on the TAD fabric. In either case, a nonwoven web can be created having apertures that align with the real physical structure of the TAD fabric, namely, with the depressed regions of a through-dried sheet. When the apertured nonwoven material is then attached to the through-dried basesheet, the apertures can be aligned with the depressed regions of the basesheet using techniques known in the art, such as photoelectric eyes or high speed CCD cameras which can view the position of apertures in the nonwoven web relative to the position of the through-dried fabric as the two are brought together, whereupon the position of one material can be adjusted both in the cross-direction and the machine direction (e.g., by controlling the speed of one layer or by machine direction motion of an unwind roll of one material) for proper placement of the two layers together.

In embodiments comprising contiguous nonwoven webs with spaced apart openings for fluid access to the hydrophilic basesheet, Applicants have found excellent fluid intake and absorbency results when the absorbent web is superposed on a separate layer of densified fluff pulp or an air laid cellulosic web, preferably an air laid web stabilized with thermosetting materials or crosslinking chemistry such as Kymene wet strength resin. With a densified cellulosic web beneath the basesheet and hydrophobic matter of the present invention, an insult of fluid that enters the hydrophilic basesheet can be pulled out of the hydrophilic basesheet by capillary suction provided that the local pore size of the underlying absorbent layer is small enough. Experiments with dyed water and also with an aqueous egg white mixture have shown that the combination of a hydrophobicly treated cellulosic basesheet resting on a densified airlaid web can result in greatly improved intake, with fluid being largely directed into the air laid material and not spreading significantly laterally in the basesheet.

It has also been discovered that highly calendered versions of such webs are suitable as hand towels. The hydrophobic, originally uppermost regions are made relatively flat, offering significant hydrophilic areas initially in contact with the wet skin for rapid intake of fluid, but also having the ability to expand after wetting to provide improved dry feel as the wet, hydrophilic areas retract from the skin relative to the more hydrophobic, elevated regions. Webs so treated can achieve the once mutually exclusive goals of having high density for economical dispensing and low density once wetted for high absorbency, while also having a dry feel in use.

Hence, in one aspect, the invention resides in an absorbent web having a dry feel when wet, comprising: (a) an inherently hydrophilic basesheet comprising papermaking fibers and having an upper surface and a lower surface, said upper surface having elevated and depressed regions; and (b) hydrophobic matter deposited preferentially on the elevated regions of the upper surface of said basesheet.

In another aspect, the invention resides in an absorbent dual-zoned web providing a dry feel in use, said web having an upper surface comprising a plurality of hydrophobically treated regions surrounded by inherently hydrophilic cellulosic regions, wherein upon wetting said web expands such that the hydrophobically treated regions are preferentially elevated relative to said hydrophilic regions.

In another aspect, the invention resides in an absorbent web having a Rewet value of about 1 g or less, comprising: (a) an inherently hydrophilic basesheet comprising papermaking fibers and having an upper surface and a lower surface, said upper surface having elevated and depressed regions with an Overall Surface Depth of 0.2 mm or greater in the uncalendered and uncreped state, said basesheet further having a Wet Compressed Bulk of at least 6 cc/g; and (b) hydrophobic matter deposited preferentially on the elevated regions of the upper surface of said basesheet.

In another aspect, the invention resides in an absorbent web having a dry feel when wet, comprising: (a) an inherently hydrophilic basesheet comprising papermaking fibers and having an upper surface and a lower surface, said upper surface having elevated and depressed regions with an Overall Surface Depth of about 0.2 mm or greater; and (b) a substantially contiguous network of hydrophobic fibers having a plurality of macroscopic openings attached to the upper surface of said basesheet such that a portion of the depressed regions of the basesheet are aligned with openings in the overlaying network of hydrophobic fibers to allow body exudates to pass through the macroscopic openings into the basesheet.

In another aspect, the invention resides in an absorbent web having a dry feel when wet, comprising: (a) an inherently hydrophilic basesheet comprising papermaking fibers and having an upper surface and a lower surface, said upper surface having elevated and depressed regions, said basesheet preferably having a wet:dry tensile ratio of at least 0.1; and (b) a contiguous network of hydrophobic matter deposited preferentially on the elevated regions of the upper surface of said basesheet.

In another aspect, the invention resides in an absorbent article comprising a liquid impermeable backsheet, a cellulosic absorbent core in superposed relation with said backsheet, and a liquid permeable absorbent web, said absorbent web comprising an inherently hydrophilic basesheet comprising papermaking fibers and having a wet:dry tensile ratio of at least 0.1, said basesheet having an upper surface and a lower surface, said upper surface having elevated and depressed regions and hydrophobic matter deposited preferentially on the elevated regions, wherein the basesheet is superposed on the absorbent core with the lower surface of the basesheet facing the absorbent core.

In another aspect, the invention resides in an absorbent article comprising a liquid impermeable backsheet, a cellulosic absorbent core in superposed relation with said backsheet, and a liquid permeable absorbent web, said absorbent web comprising an inherently hydrophilic basesheet comprising papermaking fibers, said basesheet having an upper surface and a lower surface, said upper surface having elevated and depressed regions, further comprising an apertured contiguous web of hydrophobic nonwoven material attached to the upper surface of the basesheet such that a portion of said apertures overlay the depressed regions of the basesheet, wherein the basesheet is superposed on the absorbent core with the lower surface of the basesheet facing the absorbent core.

In another aspect, the invention resides in calendered, low density structures of previously three-dimensional resilient webs having hydrophobic matter on the once uppermost regions of one or both sides of the web. Without limitation, such articles may serve as suitable hand towels by providing high initial uptake of fluid by the plurality of hydrophilic regions in the plane of the flat paper during initial wicking, followed by an enhanced dry feel as the dry-feeling treated areas rise out of the plane of the sheet during wetting. The hydrophobic matter in such articles may also be used to increase the apparent softness or lubricity of the article and be applied in contiguous or discontiguous forms.

In another aspect, the invention resides in a method for producing an intake material for an absorbent article, comprising the steps of (a) forming an embryonic paper web from an aqueous slurry of papermaking fibers; (b) through-drying the embryonic paper web on a three-dimensional through-drying fabric having a pattern of elevated and depressed regions; (c) completing the drying of the web; (d) aperturing a nonwoven web by means of hydroentangling, wherein the nonwoven web overlays a carrier fabric having substantially the same pattern of elevated and depressed regions as the through-drying fabric of step (b); and (e) joining the apertured nonwoven web with the through-dried paper web such that the apertures of the nonwoven web are substantially aligned with the depressed regions of the through-dried paper web.

In stating that hydrophobic matter is preferentially deposited on elevated portions of the basesheet, the term "preferentially" implies that more hydrophobic matter is deposited on the elevated regions rather than in the depressed regions, in terms of a mass per unit area basis, such that the depressed regions have a significantly lower amount of hydrophobic matter present than the elevated regions. It is preferred that the percentage of the hydrophobic material deposited on the elevated regions be at least about 60 percent, more specifically at least about 70 percent, and still more specifically at least about 80 percent of the total amount deposited. The hydrophobic matter can comprise fine fibers, powders, resins, gels, and other materials, preferably applied with an average superficial basis weight of less than 10 gsm, more specifically from about 1 to about 10 gsm. When used as the skin-contacting layer of absorbent articles, said absorbent web serves as an absorbent improvement over nonabsorbent, plastic apertured films or other inherently hydrophobic materials. The elevated regions of said basesheet preferably comprise between about 5 and about 300 protrusions per square inch having a height relative to the plane of the basesheet, as measured in the uncalendered state, of about 0.1 mm or greater, preferably about 0.2 mm or greater, more preferably about 0.3 mm or greater, and most preferably from about 0.25 to about 0.6 mm.

Definition of Terms and Test Procedures

In describing the webs of this invention and their fluid-handling characteristics, a number of terms and tests are used which are described below.

As used herein, "high yield pulp fibers" are those papermaking fibers of pulps produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. High yield pulps include bleached chemithermomechanical pulp (BCTMP), chemithermomechanical pulp (CTMP) pressure/pressure thermomechanical pulp (PTMP), thermomechanical pulp (TMP), thermomechanical chemical pulp (TMCP), high yield sulfite pulps, and high yield Kraft pulps, all of which contain fibers having high levels of lignin. The preferred high yield pulp fibers can also be characterized by being comprised of comparatively whole, relatively undamaged fibers, having a freeness of 250 Canadian Standard Freeness (CSF) or greater, more specifically 350 CSF or greater, and still more specifically 400 CSF or greater, and low fines content (less than 25 percent, more specifically less than 20 percent, still more specifically less that 15 percent, and still more specifically less than 10 percent by the Britt jar test). In addition to common papermaking fibers listed above, high yield pulp fibers also include other natural fibers such as milkweed seed floss fibers, abaca, hemp, kenaf, bagasse, cotton and the like.

As used herein, "wet resilient pulp fibers" are papermaking fibers selected from the group comprising high-yield fibers, chemically stiffened fibers and cross-linked fibers. Examples of chemically stiffened fibers or cross-linked fibers include mercerized fibers, HBA fibers produced by Weyerhaeuser Corp., and those such as described in U.S. Pat. No. 3,224,926, "Method of Forming Cross-linked Cellulosic Fibers and Product Thereof," issued in 1965 to L. J. Bernardin, and U.S. Pat. No. 3,455,778, "Creped Tissue Formed From Stiff Cross-linked Fibers and Refined Papermaking Fibers," issued in 1969 to L. J. Bernardin. Though any blend of wet resilient pulp fibers can be used, high-yield pulp fibers are the wet resilient fiber of choice for many embodiments of the present invention or their low cost and good fluid handling performance when used according to the principles described below.

The amount of high-yield or wet resilient pulp fibers in the basesheet can be at least about 10 dry weight percent or greater, more specifically about 15 dry weight percent or greater, more specifically about 30 dry weight percent or greater, still more specifically about 50 dry weight percent or greater, and still more specifically from about 20 to 100 percent. For layered basesheets, these same amounts can be applied to one or more of the individual layers. Because wet resilient pulp fibers are generally less soft than other papermaking fibers, in some applications it is advantageous to incorporate them into the middle of the final product, such as placing them in the center layer of a three-layered basesheet or, in the case of a two-ply product, placing them in the inwardly-facing layers of each of the two plies.

"Water retention value" (WRV) is a measure that can be used to characterize some fibers useful for purposes of this invention. WRV is measured by dispersing 0.5 grams of fibers in deionized water, soaking at least 8 hours, then centrifuging the fibers in a 1.9 inch diameter tube with a 100 mesh screen at the bottom of the tube at 1000 G for 20 minutes. The samples are weighed, then dried at 105° C. for two hours and then weighed again. WRV is (wet weight-dry weight)/dry weight. High yield pulp fibers can have a WRV of about 0.7 or greater and characteristically have a WRV of about 1 or greater and preferably from about 1 to about 2. Low-yield, cross-linked fibers typically have a Water Retention Value of less than about 1, specifically less than about 0.7 and more specifically still less than about 0.6.

"Rewet" is a measure of the amount of liquid water which can be wicked out of a moistened web into an adjacent dry filter paper and is intended to estimate the tendency of a moistened web to wet the skin. The Rewet test is performed by cutting a sample of a tissue web to a rectangle of dimensions 4 in×6 in. The test is performed in a Tappi conditioned room (50% RH, 73° F.). The initial air dry weight of the conditioned sample is recorded, then deionized water is sprayed onto both sides of the tissue sample to uniformly wet it, bringing the total wet mass of the tissue to a value of 4 times the previously recorded initial air dry weight of the sample, thus bringing the "apparent moisture ratio" of the sample to a value of 3.0 grams (±0.15 g) of added water per gram of conditioned air dry fiber. The process of repeatedly spraying and weighing the sample until the proper mass has been reached should take no more than 2 minutes. Once the sample is wetted, a single dry Whatman #3 filter, whose mass has been measured and recorded, is placed on the center of the wet tissue sample and a load is immediately placed on the filter disk. The load is a cylindrical disk of aluminum having a diameter of 4.5 inches and a thickness of 1 inch for a mass of 723 g. The aluminum disk should be centered about the filter disk. The filter paper on the wet sample remains under load for 20 seconds, at which time the load and the filter paper are immediately removed. The filter paper is then weighed, and the additional mass relative to the initial air dry mass is reported in grams as the Rewet value.

"Normalized Rewet" is the Rewet value of a sample divided by the conditioned dry mass of the sample.

"Absorbency at 0.075 psi" is a measure of basesheet absorbent capacity under a load of 0.075 psi. The test requires two metal plates cut to a length of 6 inches and a width of 4 inches. A lower plate is 0.125-inches thick and the upper plate is ¾-inch thick aluminum having a mass of 813 g, which imparts a load of 0.075 psi when placed flat on a tissue sample. The center of the upper plate has a cylindrical hole 0.25-inches in diameter. To perform the test, 4-in×6-in samples of dry tissue are cut, with the 6-in length being aligned with the machine direction. Multiple tissue plies are stacked to achieve a tissue stack weight as close to 2.8 grams as possible. The tissue stack is placed between the two horizontal plates, which lie flat in a larger tray. A titrating burette with 50 ml of deionized water is aligned directly above the hole in the upper plate. The burette is opened and water is allowed to slowly enter the hole in the upper plate such that the hole is filled with a column of water that is maintained as high as possible without rising above or spilling onto the upper surface of the plate. This is done until the sample is apparently saturated. Apparent saturation is the point at which water begins to leave any edge of the sample. The mass of water that has been removed from the burette is taken as the value for "Horizontal Absorbency at 0.075 psi." At that point, the tray containing the plates is tilted at a 45° angle for 30 seconds to allow some of the liquid in the sample to drain. The mass of any liquid that drains out is subtracted from the previous "Horizontal Absorbency at 0.075 psi" value to yield "Tilted Absorbency at 0.075 psi." For the basesheet, the horizontal absorbency at 0.075 psi can be about 5 g or greater, or alternatively 7 g or greater, 9 g or greater, 11 g or greater, or from about 6 g to about 10 g. The tilted absorbency at 0.075 psi may be about 4 g or greater, about 6 g or greater, about 8 g or greater, about 10 g or greater, or from about 6 to about 10 g. The tilted absorbency of the cover may be about 5 to 40% less than that off the basesheet alone, while the horizontal absorbency may be greater or lower than that off the basesheet.

"Fabric side" of a through-air dried paper web is the side of the web that was in contact with the through-air dryer fabric (TAD fabric) during through-drying. Typically the fabric side of a through-dried sheet offers the most pleasant tactile properties for contact with skin.

"Air side" of a through-air dried paper web is the side of the web that was not in contact with the through-air dryer fabric (TAD fabric) during through-drying. Typically the air side of a through-dried sheet feels somewhat more gritty than the fabric side of the same sheet.

"Density" can be determined by measuring the caliper of a single sheet using a TMI tester (Testing Machines, Inc., Amityville, N.Y.) with a load of 0.289 psi, e.g., using a TMI Model 49-70 with an enlarged platen. Density is calculated by dividing the caliper by the basis weight of the sheet. The basesheets useful for the purposes of this invention can have low, substantially uniform densities (high bulks), which is preferred for wet laid structures, or may have a distribution of zones of varying density, which is preferred in airlaid basesheets. Substantial density uniformity is attained, for example, by throughdrying to final dryness without differentially compressing the web. In general, the density of the basesheets of this invention can be about 0.3 gram per cubic centimeter (g/cc) or less, more specifically about 0.15 g/cc or less, still more specifically about 0.1 g/cc or less and can be from about 0.05 to 0.3 g/cc or from about 0.07 to 0.2 g/cc. It is desirable that the basesheet structure, once formed, be dried without substantially reducing the number of wet-resilient interfiber bonds. Throughdrying, which is a common method for drying tissues and towels, is a preferred method of preserving the structure. Basesheets made by wet laying followed by throughdrying typically have a density of about 0.1 gram per cubic centimeter, whereas airlaid basesheets normally used for diaper fluff typically have densities of about 0.05 gram per cubic centimeter. All of such basesheets are within the scope of this invention.

As used herein, "dry bulk" is measured with a thickness gauge having a circular platen 3 inches in diameter such that a pressure of 0.05 psi is applied to the sample, which should be conditioned at 50% relative humidity and at 73° F. for 24 hours prior to measurement. The basesheet as well as the uncalendered web can have a dry bulk of 3 cc/g or greater, preferably 6 cc/g or greater, more preferably 9 cc/g or greater, more preferably still 11 cc/g or greater, and most preferably between 8 cc/g and 28 cc/g.

"Wet strength agents" are materials used to immobilize the bonds between the fibers in the wet state. Typically the means by which fibers are held together in paper and tissue products involve hydrogen bonds and sometimes combinations of hydrogen bonds and covalent and/or ionic bonds. In the present invention, it is desirable to provide a material that will allow bonding of fibers in such a way as to immobilize the fiber to fiber bond points and make them resistant to disruption in the wet state. In this instance the wet state usually will mean when the product is largely saturated with water or other aqueous solutions, but could also mean significant saturation with body fluids such as urine, blood, mucus, menses, runny bowel movement, lymph and other body exudates.

There are a number of materials commonly used in the paper industry to impart wet strength to paper and board that are applicable to this invention. These materials are known in the art as "wet strength agents" and are commercially available from a wide variety of sources. Any material that when added to a paper web or sheet results in providing the sheet with a wet geometric tensile strength:dry geometric tensile strength ratio in excess of 0.1 will, for purposes of this invention, be termed a wet strength agent. Typically these materials are termed either as permanent wet strength agents or as "temporary" wet strength agents. For the purposes of differentiating permanent from temporary wet strength, permanent will be defined as those resins which, when incorporated into paper or tissue products, will provide a product that retains more than 50% of its original wet strength after exposure to water for a period of at least five minutes. Temporary wet strength agents are those which show less than 50% of their original wet strength after being saturated with water for five minutes. Both classes of material find application in the present invention. The amount of wet strength agent added to the pulp fibers can be at least about 0.1 dry weight percent, more specifically about 0.2 dry weight percent or greater, and still more specifically from about 0.1 to about 3 dry weight percent based on the dry weight of the fibers.

Permanent wet strength agents will provide a more or less long-term wet resilience to the structure. In contrast, the temporary wet strength agents would provide structures that had low density and high resilience, but would not provide a structure that had long-term resistance to exposure to water or body fluids. The mechanism by which the wet strength is generated has little influence on the products of this invention as long as the essential property of generating water-resistant bonding at the fiber/fiber bond points is obtained.

Suitable permanent wet strength agents are typically water soluble, cationic oligomeric or polymeric resins that are capable of either crosslinking with themselves (homocrosslinking) or with the cellulose or other constituent of the wood fiber. The most widely-used materials for this purpose are the class of polymer known as polyamide-polyamine-epichlorohydrin (PAE) type resins. These materials have been described in patents issued to Keim (U.S. Pat. Nos. 3,700,623 and 3,772,076) and are sold by Hercules, Inc., Wilmington, Del., as KYMENE 557H. Related materials are marketed by Henkel Chemical Co., Charlotte, N.C. and Georgia-Pacific Resins, Inc., Atlanta, Ga.

Polyamide-epichlorohydrin resins are also useful as bonding resins in this invention. Materials developed by Monsanto and marketed under the SANTO RES label are base-activated polyamide-epichlorohydrin resins that can be used in the present invention. These materials are described in patents issued to Petrovich (U.S. Pat. No. 3,885,158; U.S. Pat. No. 3,899,388; U.S. Pat. No. 4,129,528 and U.S. Pat. No. 4,147,586) and van Eenam (U.S. Pat. No. 4,222,921). Although they are not as commonly used in consumer products, polyethylenimine resins are also suitable for immobilizing the bond points in the products of this invention. Another class of permanent-type wet strength agents are exemplified by the aminoplast resins obtained by reaction of formaldehyde with melamine or urea.

Suitable temporary wet strength resins include, but are not limited to, those resins that have been developed by American Cyanamid and are marketed under the name PAREZ 631 NC (now available from Cytec Industries, West Paterson, N.J.). This and similar resins are described in U.S. Pat. Nos. 3,556,932 to Coscia et al. and 3,556,933 to Williams et al. Other temporary wet strength agents that should find application in this invention include modified starches such as those available from National Starch and marketed as CO-BOND 1000. It is believed that these and related starches are disclosed in U.S. Pat. No. 4,675,394 to Solarek et al. Derivatized dialdehyde starches, such as described in Japanese Kokai Tokkyo Koho JP 03,185,197, may also provide temporary wet strength. It is also expected that other temporary wet strength materials such as those described in U.S. Pat. No. 4,981,557; U.S. Pat. No. 5,008,344 and U.S. Pat. No. 5,085,736 to Bjorkquist would be of use in this invention. With respect to the classes and the types of wet strength resins listed, it should be understood that this listing is simply to provide examples and that this is neither meant to exclude other types of wet strength resins, nor is it meant to limit the scope of this invention.

Although wet strength agents as described above find particular advantage for use in connection with this invention, other types of bonding agents can also be used to provide the necessary wet resiliency. They can be applied at the wet end of the basesheet manufacturing process or applied by spraying or printing, etc. after the basesheet is formed or after it is dried.

"Noncompressive drying" refers to drying methods for drying cellulosic webs that do not involve compressive nips or other steps causing significant densification or compression of a portion of the web during the drying process. Such methods include through-air drying; air jet impingement drying; non-contacting drying such as air flotation drying, as taught by E. V. Bowden, E. V., Appita J., 44(1): 41 (1991); through-flow or impingement of superheated steam; microwave drying and other radiofrequency or dielectric drying methods; water extraction by supercritical fluids; water extraction by nonaqueous, low surface tension fluids; infrared drying; drying by contact with a film of molten metal; and other methods. It is believed that the three-dimensional basesheets of the present invention could be dried with any of the above mentioned noncompressive drying means without causing significant web densification or a significant loss of their three-dimensional structure and their wet resiliency properties. Standard dry creping technology is viewed as a compressive drying method since the web must be mechanically pressed onto part of the drying surface, causing significant densification of the regions pressed onto the heated Yankee cylinder. Technology to noncompressively dewater and dry tissue webs with an air press and optionally with a Yankee dryer operated without creping is disclosed in the following commonly owned copending applications: U.S. patent application Ser. No. unknown, "Method of Producing Low Density Resilient Webs" by F. G. Druecke et al., Attorney Docket No. 13,504, filed Oct. 31, 1997; U.S. patent application Ser. No. unknown, "Low Density Resilient Webs and Methods of Making Such Web" by S. Chen et al., Attorney Docket No. 13,381, filed Oct. 31, 1997; U.S. patent application Ser. No. 08/647,508 filed May 14, 1996 by M. A. Hermans et al. titled "Method and Apparatus for Making Soft Tissue;" and U.S. patent application Ser. No. unknown filed Oct. 31, 1997 titled "Air Press for Dewatering a Wet Web" by F. Hada et al., all of which are herein incorporated by reference. Also of potential value for the tissue making operations useful in the present invention is the paper machine disclosed in U.S. Pat. No. 5,230,776 issued Jul. 27, 1993 to I. A. Andersson et al.; and the capillary dewatering techniques disclosed in U.S. Pat. Nos. 5,598,643 issued Feb. 4, 1997 and 4,556,450 issued Dec. 3, 1985, both to S. C. Chuang et al., all of which are incorporated herein by reference. The dewatering concepts disclosed by J. D. Lindsay in "Displacement Dewatering to Maintain Bulk," *Paperi ja Puu*, 74(3): 232–242 (1992) are also of potential value.

As used herein, the "wet:dry ratio" is the ratio of the geometric mean wet tensile strength divided by the geometric mean dry tensile strength. Geometric mean tensile strength (GMT) is the square root of the product of the machine direction tensile strength and the cross-machine direction tensile strength of the web. Unless otherwise indicated, the term "tensile strength" means "geometric mean tensile strength." The basesheets of this invention preferably have a wet:dry ratio of about 0.1 or greater, more specifically about 0.15 or greater, more specifically about 0.2 or greater, still more specifically about 0.3 or greater, and still more specifically about 0.4 or greater, and still more specifically from about 0.2 to about 0.6. Tensile strengths can be measured using an Instron tensile tester using a 3-inch jaw width, a jaw span of 4 inches, and a crosshead speed of 10 inches per minute after maintaining the sample under TAPPI conditions for 4 hours before testing. For enhanced wet resiliency and integrity, the basesheets of this invention also preferably have a minimum absolute ratio of dry tensile strength to basis weight of about 1 gram/gsm, preferably from about 2 grams/gsm, more preferably about 5 grams/gsm, more preferably about 10 grams/gsm and still more preferably about 20 grams/gsm and preferably from about 15 to 50 grams/gsm.

"Overall Surface Depth". A three-dimensional basesheet or web is a sheet with significant variation in surface elevation due to the intrinsic structure of the sheet itself. As used herein, this elevation difference is expressed as the "Overall Surface Depth." The basesheets useful for this invention possess three-dimensionality and have an Overall Surface Depth of about 0.1 mm. or greater, more specifically about 0.3 mm. or greater, still more specifically about 0.4 mm. or greater, still more specifically about 0.5 mm. or greater, and still more specifically from about 0.4 to about 0.8 mm.

The three-dimensional structure of a largely planar sheet can be described in terms of its surface topography. Rather than presenting a nearly flat surface, as is typical of conventional paper, the molded sheets useful in producing the present invention have significant topographical structures that, in one embodiment, may derive in part from the use of sculptured through-drying fabrics such as those taught by Chiu et al. in U.S. Pat. No. 5,429,686, previously incorporated by reference. The resulting basesheet surface topography typically comprises a regular repeating unit cell that is typically a parallelogram with sides between 2 and 20 mm in length. For wetlaid materials, it is preferred that these three-dimensional basesheet structures be created by molding the moist sheet or be created prior to drying, rather than by creping or embossing or other operations after the sheet has been dried. In this manner, the three-dimensional basesheet structure is more likely to be well-retained upon wetting, helping to provide high wet resiliency and to promote good in-plane permeability. For air-laid basesheets, the structure may be imparted by thermal embossing of a fibrous mat with binder fibers that are activated by heat. For example, an air-laid fibrous mat containing thermoplastic or hotmelt binder fibers may be heated and then embossed before the structure cools to permanently give the sheet a three-dimensional structure.

In addition to the regular geometrical structure imparted by the sculptured fabrics and other fabrics used in creating a basesheet, additional fine structure, with an in-plane length scale less than about 1 mm, can be present in the basesheet. Such a fine structure can stem from microfolds created during differential velocity transfer of the web from one fabric or wire to another prior to drying. Some of the materials of the present invention, for example, appear to have fine structure with a fine surface depth of 0.1 mm or greater, and sometimes 0.2 mm or greater, when height profiles are measured using a commercial moiré interferometer system. These fine peaks have a typical half-width less than 1 mm. The fine structure from differential velocity transfer and other treatments may be useful in providing additional softness, flexibility, and bulk. Measurement of the surface structures is described below.

An especially suitable method for measurement of Overall Surface Depth is moiré interferometry, which permits accurate measurement without deformation of the surface. For reference to the materials of the present invention, surface topography should be measured using a computer-controlled white-light field-shifted moiré interferometer with about a 38 mm field of view. The principles of a useful implementation of such a system are described in Bieman et al. (L. Bieman, K. Harding, and A. Boehnlein, "Absolute Measurement Using Field-Shifted Moiré," SPIE Optical Conference Proceedings, Vol. 1614, pp. 259–264, 1991). A suitable commercial instrument for moiré interferometry is the CADEYES® interferometer produced by Medar, Inc. (Farmington Hills, Mich.), constructed for a 38-mm field-of-view (a field of view within the range of 37 to 39.5 mm is adequate). The CADEYES® system uses white light which is projected through a grid to project fine black lines onto the sample surface. The surface is viewed through a similar grid, creating moiré fringes that are viewed by a CCD camera. Suitable lenses and a stepper motor adjust the optical configuration for field shifting (a technique described below). A video processor sends captured fringe images to a PC computer for processing, allowing details of surface height to be back-calculated from the fringe patterns viewed by the video camera.

In the CADEYES moiré interferometry system, each pixel in the CCD video image is said to belong to a moiré fringe that is associated with a particular height range. The method of field-shifting, as described by Bieman et al. (L. Bieman, K. Harding, and A. Boehnlein, "Absolute Measurement Using Field-Shifted Moiré," SPIE Optical Conference Proceedings, Vol. 1614, pp. 259–264, 1991) and as originally patented by Boehnlein (U.S. Pat. No. 5,069,548, herein incorporated by reference), is used to identify the fringe number for each point in the video image (indicating which fringe a point belongs to). The fringe number is needed to determine the absolute height at the measurement point relative to a reference plane. A field-shifting technique (sometimes termed phase-shifting in the art) is also used for sub-fringe analysis (accurate determination of the height of the measurement point within the height range occupied by its fringe). These field-shifting methods coupled with a camera-based interferometry approach allows accurate and rapid absolute height measurement, permitting measurement to be made in spite of possible height discontinuities in the surface. The technique allows absolute height of each of the roughly 250,000 discrete points (pixels) on the sample surface to be obtained, if suitable optics, video hardware, data acquisition equipment, and software are used that incorporates the principles of moiré interferometry with field-shifting. Each point measured has a resolution of approximately 1.5 microns in its height measurement.

The computerized interferometer system is used to acquire topographical data and then to generate a grayscale image of the topographical data, said image to be hereinafter called "the height map." The height map is displayed on a computer monitor, typically in 256 shades of gray and is quantitatively based on the topographical data obtained for the sample being measured. The resulting height map for the 38-mm square measurement area should contain approximately 250,000 data points corresponding to approximately 500 pixels in both the horizontal and vertical directions of the displayed height map. The pixel dimensions of the height map are based on a 512×512 CCD camera which provides images of moiré patterns on the sample which can be analyzed by computer software. Each pixel in the height map represents a height measurement at the corresponding x- and y-location on the sample. In the recommended system, each pixel has a width of approximately 70 microns, i.e. represents a region on the sample surface about 70 microns long in both orthogonal in-plane directions). This level of resolution prevents single fibers projecting above the surface from having a significant effect on the surface height measurement. The z-direction height measurement must have a nominal accuracy of less than 2 microns and a z-direction range of at least 1.5 mm. (For further background on the measurement method, see the CADEYES Product Guide, Medar, Inc., Farmington Hills, Mich., 1994, or other CADEYES manuals and publications of Medar, Inc.) The CADEYES system can measure up to 8 moiré fringes, with each fringe being divided into 256 depth counts (sub-fringe height increments, the smallest resolvable height difference). There will be 2048 height counts over the measurement range. This determines the total z-direction range, which is approximately 3 mm in the 38-mm field-of-view instrument. If the height variation in the field of view covers more than eight fringes, a wrap-around effect occurs, in which the ninth fringe is labeled as if it were the first fringe and the tenth fringe is labeled as the second, etc. In other words, the measured height will be shifted by 2048 depth counts. Accurate measurement is limited to the main field of 8 fringes.

The moiré interferometer system, once installed and factory calibrated to provide the accuracy and z-direction range stated above, can provide accurate topographical data for materials such as paper towels. (Those skilled in the art may confirm the accuracy of factory calibration by performing measurements on surfaces with known dimensions.) Tests are performed in a room under Tappi conditions (73° F., 50% relative humidity). The sample must be placed flat on a surface lying aligned or nearly aligned with the measurement plane of the instrument and should be at such a height that both the lowest and highest regions of interest are within the measurement region of the instrument.

Once properly placed, data acquisition is initiated using Medar's PC software and a height map of 250,000 data points is acquired and displayed, typically within 30 seconds from the time data acquisition was initiated. (Using the CADEYES® system, the "contrast threshold level" for noise rejection is set to 1, providing some noise rejection without excessive rejection of data points.) Data reduction and display are achieved using CADEYES® software for PCs, which incorporates a customizable interface based on Microsoft Visual Basic Professional for Windows (version 3.0). The Visual Basic interface allows users to add custom analysis tools.

The height map of the topographical data can then be used by those skilled in the art to identify characteristic unit cell structures (in the case of structures created by fabric patterns; these are typically parallelograms arranged like tiles to cover a larger two-dimensional area) and to measure the typical peak to valley depth of such structures. A simple method of doing this is to extract two-dimensional height profiles from lines drawn on the topographical height map which pass through the highest and lowest areas of the unit cells. These height profiles can then be analyzed for the peak to valley distance, if the profiles are taken from a sheet or portion of the sheet that was lying relatively flat when measured. To eliminate the effect of occasional optical noise and possible outliers, the highest 10% and the lowest 10% of the profile should be excluded, and the height range of the remaining points is taken as the surface depth. Technically, the procedure requires calculating the variable which we term "P10," defined at the height difference between the 10% and 90% material lines, with the concept of material lines being well known in the art, as explained by L. Mummery, in *Surface Texture Analysis*: The Handbook, Hommelwerke GmbH, Mühlhausen, Germany, 1990. In this approach, which will be illustrated with respect to FIG. 7, the surface 31 is viewed as a transition from air 32 to material 33. For a given profile 30, taken from a flat-lying sheet, the greatest height at which the surface begins—the height of the highest peak—is the elevation of the "0% reference line" 34 or the "0% material line," meaning that 0% of the length of the horizontal line at that height is occupied by material. Along the horizontal line passing through the lowest point of the profile, 100% of the line is occupied by material, making that line the "100% material line" 35. In between the 0% and 100% material lines (between the maximum and minimum points of the profile), the fraction of horizontal line length occupied by material will increase monotonically as the line elevation is decreased. The material ratio curve z gives the relationship between material fraction along a horizontal line passing through the profile and the height of the line. The material ratio curve is also the cumulative height distribution of a profile. (A more accurate term might be "material fraction curve.")

Once the material ratio curve is established, one can use it to define a characteristic peak height of the profile. The P10 "typical peak-to-valley height" parameter is defined as the difference 37 between the heights of the 10% material line 38 and the 90% material line 39. This parameter is relatively robust in that outliers or unusual excursions from the typical profile structure have little influence on the P10 height. The units of P10 are mm. The Overall Surface Depth of a material is reported as the P10 surface depth value for profile lines encompassing the height extremes of the typical unit cell of that surface. "Fine surface depth" is the P10 value for a profile taken along a plateau region of the surface which is relatively uniform in height relative to profiles encompassing a maxima and minima of the unit cells. Measurements are reported for the most textured side of the basesheets of the present invention, which is typically the side that was in contact with the through-drying fabric when air flow is toward the through-dryer. FIG. 8 represents a profile of Example 13 of the present invention, discussed below, having an Overall Surface Depth of about 0.5.

Overall Surface Depth is intended to examine the topography produced in the basesheet, especially those features created in the sheet prior to and during drying processes, but is intended to exclude "artificially" created large-scale topography from dry converting operations such as embossing, perforating, pleating, etc. Therefore, the profiles examined should be taken from unembossed regions if the basesheet has been embossed, or should be measured on an unembossed basesheet. Overall Surface Depth measurements should exclude large-scale structures such as pleats or folds which do not reflect the three-dimensional nature of the original basesheet itself. It is recognized that sheet topography may be reduced by calendering and other operations which affect the entire basesheet. Overall Surface Depth measurement can be appropriately performed on a calendered basesheet.

The "Wet Wrinkle Recovery Test" is a slight modification of AATCC Test Method 66–1990 taken from the Technical Manual of the American Association of Textile Chemists and Colorists (1992), page 99. The modification is to first wet the samples before carrying out the method. This is done by soaking the samples in water containing 0.01 percent TRITON X-100 wetting agent (Rohm & Haas) for five minutes before testing. Sample preparation is carried out at 73° F. and 50 percent relative humidity. The sample is gently removed from the water with a tweezers, drained by pressing between two pieces of blotter paper with 325 grams of weight, and placed in the sample holder to be tested as with the dry wrinkle recovery test method. The test measures the highest recovery angle of the sample being tested (in any direction, including the machine direction and the cross-machine direction), with 180° representing total recovery. The Wet Wrinkle Recovery, expressed as a percent recovery, is the measured recovery angle divided by 180°, multiplied by 100. Basesheets of this invention can exhibit a Wet Wrinkle Recovery of about 60 percent or greater, more specifically about 70 percent or greater, and still more specifically about 80 percent or greater.

"Wet compressive resiliency" of the basesheets is defined by several parameters and can be demonstrated using a materials property procedure that encompasses both wet and dry characteristics. A programmable strength measurement device is used in compression mode to impart a specified series of compression cycles to an initially dry, conditioned sample, after which the sample is carefully moistened in a specified manner and subjected to the same sequence of compression cycles. While the comparison of wet and dry properties is of general interest, the most important information from this test concerns the wet properties. The initial testing of the dry sample can be viewed as a conditioning step. The test sequence begins with compression of the dry sample to 0.025 psi to obtain an initial thickness (cycle A), then two repetitions of loading up to 2 psi followed by unloading (cycles B and C). Finally, the sample is again compressed to 0.025 psi to obtain a final thickness (cycle D). (Details of the procedure, including compression speeds, are given below). Following the treatment of the dry sample, moisture is applied uniformly to the sample using a fine mist of deionized water to bring the moisture ratio (g water/g dry fiber) to approximately 1.1. This is done by applying 95–110% added moisture, based on the conditioned sample mass. This puts typical cellulosic materials in a moisture range where physical properties are relatively insensitive to moisture content (e.g., the sensitivity is much less than it is for moisture ratios less than 70%). The moistened sample is then placed in the test device and the compression cycles are repeated.

Three measures of wet resiliency are considered which are relatively insensitive to the number of sample layers used in the stack. The first measure is the bulk of the wet sample at 2 psi. This is referred to as the "Wet Compressed Bulk" (WCB). The second measure is termed "Wet Springback Ratio" (WS), which is the ratio of the moist sample thickness at 0.025 psi at the end of the compression test (cycle D) to the thickness of the moist sample at 0.025 psi measured at the beginning of the test (cycle A). The third measure is the "Loading Energy Ratio" (LER), which is the ratio of loading energy in the second compression to 2 psi (cycle C) to that of the first compression to 2 psi (cycle B) during the sequence described above, for a wetted sample. The final wet bulk measured at the end of the test (at 0.025 psi) is termed the "final bulk" or "FB" value. When load is plotted as a function of thickness, loading energy is the area under the curve as the sample goes from an unloaded state to the peak load of that cycle. For a purely elastic material, the springback and loading energy ratio would be unity. Applicants have found that the three measures described here are relatively independent of the number of layers in the stack and serve as useful measures of wet resiliency. Also referred to herein is the "Compression Ratio", which is defined as the ratio of moistened sample thickness at peak load in the first compression cycle to 2 psi to the initial moistened thickness at 0.025 psi.

In carrying out the foregoing measurements of the wet compressive resiliency, samples should be conditioned for at least 24 hours under TAPPI conditions (50% RH, 73° F.). Specimens are die cut to 2.5"×2.5" squares. Conditioned sample weight should be near 0.4 g, if possible, and within the range of 0.25 to 0.6 g for meaningful comparisons. The target mass of 0.4 g is achieved by using a stack of 2 or more sheets if the sheet basis weight is less than 65 gsm. For example, for nominal 30 gsm sheets, a stack of 3 sheets will generally be near 0.4 g total mass.

Compression measurements are performed using an Instron 4502 Universal Testing Machine interfaced with a 286 PC computer running Instron Series XII software (1989 issue) and Version 2 firmware. The standard "286 computer" referred to has an 80286 processor with a 12 MHz clock speed. The particular computer used was a Compaq DeskPro 286e with an 80287 math coprocessor and a VGA video adapter. A 1 kN load cell is used with 2.25" diameter circular platens for sample compression. The lower platen has a ball bearing assembly to allow exact alignment of the platens. The lower platen is locked in place while under load (30–100 lbf) by the upper platen to ensure parallel surfaces. The upper platen must also be locked in place with the standard ring nut to eliminate play in the upper platen as load is applied.

Following at least one hour of warm-up after start-up, the instrument control panel is used to set the extensionometer to zero distance while the platens are in contact (at a load of 10–30 lb). With the upper platen freely suspended, the calibrated load cell is balanced to give a zero reading. The extensionometer and load cell should be periodically checked to prevent baseline drift (shirting of the zero points). Measurements must be performed in a controlled humidity and temperature environment, according to TAPPI specifications (50%±2% RH and 73° F.). The upper platen is then raised to a height of 0.2 in. and control of the Instron is transferred to the computer.

Using the Instron Series XII Cyclic Test software with a 286 computer, an instrument sequence is established with 7 markers (discrete events) composed of 3 cyclic blocks (instructions sets) in the following order:

Marker 1:Block 1
Marker 2:Block 2
Marker 3:Block 3
Marker 4:Block 2
Marker 5:Block 3
Marker 6:Block 1
Marker 7:Block 3.

Block 1 instructs the crosshead to descend at 1.5 in./min. until a load of 0.1 lb. is applied (the Instron setting is −0.1 lb., since compression is defined as negative force). Control is by displacement. When the targeted load is reached, the applied load is reduced to zero.

Block 2 directs that the crosshead range from an applied load of 0.05 lb. to a peak of 8 lb. then back to 0.05 lb. at a speed of 0.4 in./min. Using the Instron software, the control mode is displacement, the limit type is load, the first level is −0.05 lb., the second level is −8 lb., the dwell time is 0 sec., and the number of transitions is 2 (compression, then relaxation); "no action" is specified for the end of the block.

Block 3 uses displacement control and limit type to simply raise the crosshead to 0.2 in. at a speed of 4 in./min., with 0 dwell time. Other Instron software settings are 0 in first level, 0.2 in second level, 1 transition, and "no action" at the end of the block.

When executed in the order given above (Markers 1–7), the Instron sequence compresses the sample to 0.025 psi (0.1 lbf), relaxes, then compresses to 2 psi (8 lbs.), followed by decompression and a crosshead rise to 0.2 in., then compress the sample again to 2 psi, relaxes, lifts the crosshead to 0.2 in., compresses again to 0.025 psi (0.1 lbf), and then raises the crosshead. Data logging should be performed at intervals no greater than every 0.02" or 0.4 lb. (whichever comes first) for Block 2 and for intervals no greater than 0.01 lb. for Block 1. Preferably, data logging is performed every 0.004 lb. in Block 1 and every 0.05 lb. or 0.005 in. (whichever comes first) in Block 2.

The results output of the Series XII software is set to provide extension (thickness) at peak loads for Markers 1, 2, 4 and 6 (at each 0.025 and 2.0 psi peak load), the loading energy for Markers 2 and 4 (the two compressions to 2.0 psi previously termed cycles B and C, respectively), the ratio of the two loading energies (second cycle/first cycle), and the ratio of final thickness to initial thickness (ratio of thickness at last to first 0.025 psi compression). Load versus thickness results are plotted on the screen during execution of Blocks 1 and 2.

In performing a measurement, the dry, conditioned sample is centered on the lower platen and the test is initiated. Following completion of the sequence, the sample is immediately removed and moisture (deionized water at 72–73° F.) is applied. Moisture is applied uniformly with a fine mist to reach a moist sample mass of approximately 2.0 times the initial sample mass (95–110% added moisture is applied, preferably 100% added moisture, based on conditioned sample mass; this level of moisture should yield an absolute moisture ratio of about 1.1 g. water/g. oven dry fiber—with oven dry referring to drying for at least 30 minutes in an oven at 105° C.). (For the uncreped through-dried materials of this invention, the moisture ratio could be within the range of 1.05 to 1.7 without significantly affecting the results). The mist should be applied uniformly to separated sheets (for stacks of more than 1 sheet), with spray applied to both front and back of each sheet to ensure uniform moisture application. This can be achieved using a conventional plastic spray bottle, with a container or other barrier blocking most of the spray, allowing only about the upper 10–20% of the spray envelope—a fine mist—to approach the sample. The spray source should be at least 10" away from the sample during spray application. In general, care must be applied to ensure that the sample is uniformly moistened by a fine spray. The sample must be weighed several times during the process of applying moisture to reach the targeted moisture content. No more than three minutes should elapse between the completion of the compression test on the dry sample and the completion of moisture application. Allow 45–60 seconds from the final application of spray to the beginning of the subsequent compression test to provide time for internal wicking and absorption of the spray. Between three and four minutes will elapse between the completion of the dry compression sequence and initiation of the wet compression sequence.

Once the desired mass range has been reached, as indicated by a digital balance, the sample is centered on the lower Instron platen and the test sequence is initiated. Following the measurement, the sample is placed in a 105° C. oven for drying, and the oven dry weight will be recorded later (sample should be allowed to dry for 30–60 minutes, after which the dry weight is measured).

Note that creep recovery can occur between the two compression cycles to 2 psi, so the time between the cycles may be important. For the instrument settings used in these Instron tests, there is a 30 second period (±4 sec.) between the beginning of compression during the two cycles to 2 psi. The beginning of compression is defined as the point at which the load cell reading exceeds 0.03 lb. Likewise, there is a 5–8 second interval between the beginning of compression in the first thickness measurement (ramp to 0.025 psi) and the beginning of the subsequent compression cycle to 2 psi. The interval between the beginning of the second compression cycle to 2 psi and the beginning of compression for the final thickness measurement is approximately 20 seconds.

The utility of a web or absorbent structure having a high Wet Compressed Bulk (WCB) value is obvious, for a wet material which can maintain high bulk under compression can maintain higher fluid capacity and is less likely to allow fluid to be squeezed out when it is compressed.

High Wet Springback Ratio values are especially desirable because a wet material that springs back after compression can maintain high pore volume for effective intake and distribution of subsequent insults of fluid, and such a material can regain fluid during its expansion which may have been expelled during compression. In diapers, for example, a wet region may be momentarily compressed by body motion or changes in body position. If the material is unable to regain its bulk when the compressive force is released, its effectiveness for handling fluid is reduced.

High Loading Energy Ratio values in a material are also useful, for such a material continues to resist compression (LER is based on a measure of the energy required to compress a sample) at loads less than the peak load of 2 psi, even after it has been heavily compressed once. Maintaining such wet elastic properties is believed to contribute to the feel of the material when used in absorbent articles, and may help maintain the fit of the absorbent article against the wearer's body, in addition to the general advantages accrued when a structure can maintain its pore volume when wet.

The hydrophobically-treated absorbent webs of this invention and the untreated, inherently hydrophilic basesheets useful in producing this invention can exhibit one or more of the foregoing properties. More specifically, said absorbent webs and basesheets can have a Wet Compressed Bulk of about 6 cubic centimeters per gram or greater, more specifically about 7 cubic centimeters per gram or greater, more specifically about 8 cubic centimeters per gram or greater, and still more specifically from about 8 to about 13 cubic centimeters per gram. The Compression Ratio can be about 0.7 or less, more specifically about 0.6 or less, still more specifically about 0.5 or less, and still more specifically from 0.4 to about 0.7. Also, they can have a Wet Springback Ratio of about 0.6 or greater, more specifically about 0.7 or greater, more specifically about 0.85, and still more specifically from about 0.8 to about 0.93. The Loading Energy Ratio can be about 0.6 or greater, more specifically 0.7 or greater, more specifically still about 0.8 or greater, and most specifically from about 0.75 to about 0.9. Final bulk can be about 8 cubic centimeters per gram or greater or preferably about 12 centimeters per gram or greater.

"In-Plane Permeability". An important property of porous media, particularly for absorbent products, is the permeability to liquid flow. The complex, interconnected pathways between the solid particles and boundaries of a porous media provide routes for fluid flow which may offer significant flow resistance due to the narrowness of the channels and the tortuosity of the pathways.

For paper, permeability is commonly expressed in terms of gas flow rates through a sheet. This practice is useful for comparing similar sheets, but does not truly characterize the interaction of flowing fluid with the porous structure and provides no direct information about flow in a wet sheet. The standard engineering definition of permeability provides a more useful parameter, though one less easily measured. The standard definition is based on Darcy's law (see F. A. L. Dullien, *Porous Media: Fluid Transport and Pore Structure*, Academic Press, New York, 1979), which, for one-dimensional flow, states that the velocity of fluid flow through a saturated porous medium is directly proportional to the pressure gradient:

$$V = \frac{K}{\mu}\frac{\Delta P}{L} \tag{1}$$

where V is the superficial velocity (flow rate divided by area), K is the permeability, $\mu$ is the fluid viscosity, and $\Delta P$ is the pressure drop in the flow direction across a distance L. The units of K are $m^2$. In Equation (1), the permeability is an empirical proportionality parameter linking fluid velocity to pressure drop and viscosity. For a homogeneous medium, K is not a function of $\Delta P$, sample length, or viscosity, but is an intrinsic parameter describing the flow resistance of the medium. In a compressible medium, permeability will be a function of the degree of compression. Darcian permeability is a fundamental parameter for processes involving fluid flow in fibrous webs.

Darcian permeability has units of area ($m^2$) and for simple uniform cylindrical pores is proportional to the cross sectional area of a single pore. However, the permeability of most real materials cannot be predicted from an optical assessment of pore size. Permeability is determined not only by pore size, but also pore orientation, tortuosity, and interconnectedness. Large pores in the body of an object may be inaccessible to fluid flow or accessible only through minute pores offering high flow resistance. Even with a full three-dimensional description of the pore space of a material from x-ray tomography or other imaging techniques, it is difficult to predict or calculate the permeability. Permeability and pore size determinations are related but distinct pieces of information about a material. For example, a sheet of metal with discreet, nonoverlapping holes punched in it may have very large pores (the holes), while still having negligible In-Plane Permeability. Swiss cheese has many large pores, but typically has negligible permeability in any direction unless sliced so thin that individual holes can extend from one face to the other of the cheese sample.

Most studies of permeability in paper have focused on flow in the z-direction (normal to the plane of the sheet), which is of practical importance in wet pressing and other unit operations. However, paper is an anisotropic material (for example, see E. L. Back, "The Pore Anisotropy of Paper Products and Fibre Building Boards," Svensk Papperstidning, 69:219 (1966)), meaning that fluid flow properties are a function of direction. In this case, different flow directions will appear to have different apparent permeabilities. The many possibilities of flow direction and pressure gradients in such a medium can be encompassed with a multidimensional form of Darcy's law, $$\overline{v} = \frac{-\overline{\overline{K}} \cdot \nabla P}{\mu}, \quad (2)$$

where $\overline{v}$ is the superficial velocity vector (volumetric flow rate divided by cross-sectional area of the flow), $\mu$ is the viscosity of the fluid, $\overline{\overline{K}}$ is a second-order tensor and $\nabla P$ is the pressure gradient. If a Cartesian coordinate system is chosen to correspond with the principal flow directions of the porous medium, then the permeability tensor becomes a diagonal matrix (see Jacob Bear, "Dynamics of Fluids in Porous Media.," American Elsevier, New York, N.Y., 1972, pp. 136–151):

$$\overline{\overline{K}} = \begin{bmatrix} K_x & 0 & 0 \\ 0 & K_y & 0 \\ 0 & 0 & K_z \end{bmatrix}, \quad (3)$$

where $K_x$, $K_y$, and $K_z$ are the principal permeability components in the x-, y-, and z-directions, respectively. In paper, these directions will generally correspond to the cross-direction (taken here as y) and the machine-direction (taken as x, the direction of maximum In-Plane Permeability) in the plane, and the transverse or thickness direction (z). Thus, the anisotropic permeability of typical machine-made paper can be characterized with three permeability parameters, one for the machine-direction, one for the cross-direction, and one for the z-direction. (In some cases, as when there are unbalanced flows in the headbox of the paper machine, the direction of maximum permeability may be slightly off from the machine direction; the direction of maximum In-Plane Permeability and the direction orthogonal to that should be used for the x- and y-directions, respectively, in that case.) In handsheets, there may be no preferential direction of orientation for fibers lying in the plane, so the x- and y-direction permeability values should be equal (in other words, such a sheet is isotropic in the plane).

In spite of the past focus on z-direction permeability in paper, In-Plane Permeability (both $K_x$ and $K_y$ are in-plane factors) is important in a variety of applications, especially in absorbent articles. Body fluids or other liquids flowing into the absorbent article usually enter the article in a narrow, localized region. Efficient use of the absorbent medium requires that the incoming fluid be distributed laterally through in-plane flow in the absorbent article, otherwise the local capacity of the article to handle the incoming liquid may be overwhelmed resulting in leakage and poor utilization of the absorbent core. The ability of fluid to flow in the plane of the article is a function of the driving force for fluid flow, which can be a combination of capillary wicking and hydraulic pressure from fluid source, and of the ability of the porous medium to conduct flow, which is described in large part by the Darcian permeability of the material. Two-phase flow and non-Newtonian liquids or suspensions complicate the physics, but the in-plane permeability of the porous medium is a critical factor for rapid in-plane distribution of liquid insults. Especially in the case of urine management, where liquid flow rates may occur far in excess of the ability of capillary forces, high In-Plane Permeability is needed in the intake layer to allow the fluid to be distributed laterally rather than to leak.

While many past studies of liquid permeability in paper focused exclusively on measuring $K_z$ for z-direction flow, more recently, methods have been taught for measuring permeability in the plane of a paper sheet. J. D. Lindsay and P. H. Brady teach methods for in-plane and z-direction permeability measurements of saturated paper in "Studies of Anisotropic Permeability with Applications to Water Removal in Fibrous Webs: Part I," Tappi J., 76(9): 119–127 (1993) and "Studies of Anisotropic Permeability with Applications to Water Removal in Fibrous Webs: Part II," Tappi J., 76(11): 167–174 (1993). Related methods have been published by K. L. Adams, B. Miller, and L. Rebenfeld in "Forced In-Plane Flow of an Epoxy Resin in Fibrous Networks," Polymer Engineering and Science, 26(20): 1434–1441 (1986); J. D. Lindsay in "Relative Flow Porosity in Fibrous Media: Measurements and Analysis, Including Dispersion Effects," Tappi J., 77(6): 225–239 (June 1994); J. D. Lindsay and J. R. Wallin, "Characterization of In-Plane Flow in Paper," AIChE 1989 and 1990 Forest Products Symposium, Tappi Press, Atlanta, Ga. (1992), p. 121; and D. H. Horstmann, J. D. Lindsay, and R. A. Stratton, "Using Edge-Flow Tests to Examine the In-Plane Anisotropic Permeability of Paper," Tappi J., 74(4): 241 (1991).

The basic method used in most of these publications is injection of fluid into the center of a paper disk that is constrained between two flat surfaces to force the fluid flow to be in the radial direction, proceeding from the injection point at the center of the disk to the outer edge of the disk. This is illustrated in FIG. 9, which depicts a sheet 41 in which a central hole 42 has been punched and into which fluid is injected by means of an injection port of the same size as the punched hole. Fluid is forced to flow to the outer radial edge 43. For a liquid-saturated sheet of constant thickness subject to steady radial fluid flow in the manner described in the work of Lindsay and others, the equation relating average In-Plane Permeability to fluid flow is:

$$K_r \equiv \frac{K_x + K_y}{2} = \frac{Q\mu \ln(R_o / R_i)}{2\pi L_p \Delta P}, \quad (4)$$

where $R_o$ is the radius of the paper disk 41, $R_i$ is the radius of the central hole 42 in the sample into which fluid is injected through an injection port; $L_p$ is the thickness of the paper; $\Delta P$ is the constant pressure above atmospheric pressure at which fluid is injected into the disk (the gauge pressure at the injection pore); Q is the volumetric flow rate of liquid, and $K_r$ is the In-Plane Permeability, technically the average radial permeability, defined as the average of the two in-plane permeability components. The disk diameter is 5 inches. The central inlet hole 42 was consistently 0.375 inches (⅜ inch) and was created using a paper punch tool.

The test apparatus for In-Plane Permeability measurements is depicted in FIG. 10 and FIG. 11, which is similar in principle to the apparatus taught by Lindsay and Brady, previously cited. Tubing 45 connects water from a water reservoir to an injection port drilled into a 1-inch thick Plexiglas support plate 45. (The support plate is transparent to permit viewing of the wetted sample, especially in cases when an aqueous dye solution is injected into the sample. A mirror at a 45 degree angle below the support plate facilitates viewing and photography.) The water reservoir 51 provides a nearly constant hydraulic head 49 for fluid injection during the test. The volumetric flow rate is obtained by noting the change in water reservoir mass as a function of time, and converting the water mass flow rate to a volumetric flow rate. Vacuum-deaerated deionized water at room temperature is used.

In using the apparatus, a paper disk 41, cut to be 5-inches in diameter and having a central hole diameter of 0.375-inches, is placed on the support plate 46 over the injection port 44 (0.375 inches diameter also) and is then saturated with water. The fluid injection line 45 and the injection port 44 should be filled with water and efforts should be taken to avoid air bubbles being trapped in the sheet or in the injection area. To help eliminate air pockets, the sample 41 should be bent gently in the center as it is placed on the wet support plate to initiate liquid contact in the center of the sample; the edges can then be lowered gradually to create a wedge-like motion of the liquid meniscus to sweep air bubbles out from under the sheet. Multi-ply stacks of sheets can be handled in the same way, although preliminary sample wetting may be needed to remove interply air bubbles. The goal in removing air bubbles is to reduce the flow blockage that trapped air bubbles can cause.

Once the wetted sample is in place, a cylindrical metal platen 47, 5-inches in diameter, is gently lowered on top of the sample to provide a constant compressive load and to provide a reference surface on its top for thickness measurement with displacement gauges 48. Three displacement gauges 48 are used, spaced approximately evenly around the edge of the top of the metal cylinder 47, in order to measure the average thickness of the sheet 41. The sample thickness is taken as the average of the three displacement values relative to a zero point when no sample is present. A suitable thickness gauge is the Mitutoyo Digimatic Indicator, Model 543-525-1, with a 2-inch stroke (traveling distance of the contacting spindle) and a precision of 1 micrometer. The thickness gauges are rigidly mounted relative to the support plate. The contacting spindles of the thickness gauges can be raised and lowered (without changing the position of the body of the gauge) by use of a cable to provide clearance for moving the metal platen onto the sample. The small force applied by the thickness gauges 48 should be added to the weight of the metal platen 47 to obtain the total force applied to the sample 41; this force, when divided by the cross sectional area of the sample and platen, should be 0.8 psi.

A hydraulic head of 13 inches is used to drive the liquid flow. The head is the vertical distance 49 between the water line 50 of the supply reservoir 51 and the plane of the sample 41. This head is achieved by placement of a water bottle 51, filled to a specified level 50, on a mass balance 52 at a fixed height relative to the support plate 46 on which the sample rests. As the sample is being placed on the support plate, the water reservoir is at such a height that the water level 50 in the reservoir is nearly the same as (or slightly greater than) the support plate 46 on which the sample rests. When the sample has been moistened and placed under the compressive load of the metal platen, the water reservoir is then raised and placed on a mass balance 52 such that the water level is 13 inches above the support platen. A timer is activated and the water reservoir mass is recorded at 20 seconds or 30 seconds intervals for a least 90 seconds. The thickness readings of the three gauges is also recorded regularly during the test. To reduce creep, the saturated sample should be allowed to equilibrate under the compressive load for at least 30 seconds before the water bottle is raised and forced flow through the sample begins.

The change in water reservoir mass as a function of time gives the mass flow rate, which can easily be converted to a volumetric flow rate for use in Equation 4. Normal engineering principles should be used to ensure that the proper units (preferably SI units) are used in applying Equation 4.

In performing In-Plane Permeability measurements, it is important that the sample be uniformly compressed against the restraining surfaces to prevent large channels or openings that would provide paths of least resistance for substantial liquid flow that could bypass much of the sample itself. Ideally, the liquid will flow uniformly through the sample, and this can be ascertained by injecting dyed fluid into the sample and observing the shape of the dyed region through the transparent support plate. Injected dye should spread out uniformly from the injection point. In isotropic samples, the shape of the moving dye region should be nearly circular. In materials with in-plane anisotropy due to fiber orientation or small-scale structural orientation, the shape of the dye region should be oval or elliptical, and nearly symmetric about the injection point. A suitable dye for such tests is Versatint Purple II made by Milliken Chemical Corp. (Inman, S.C.). This is a fugitive dye that does not absorb onto cellulose, allowing for easy visualization of liquid flow through the fibrous medium.

As will be illustrated in the Examples, the webs and basesheets of this invention possess very high In-Plane Permeability. The In-Plane Permeability can be about $0.1 \times 10^{-10}$ square meters or greater, more specifically about $0.3 \times 10^{-10}$ square meters or greater, more specifically about $0.5 \times 10^{-10}$ square meters or greater, still more specifically from about $0.5 \times 10^{-10}$ to about $8 \times 10^{-10}$ square meters, and still more specifically from about $0.8 \times 10^{-10}$ to about $5 \times 10^{-10}$ square meters.

BRIEF DESCRIPTION OF THE DRAWINGS

FIG. 5 depicts a version of FIG. 2 in which the low regions of the basesheet are provided with apertures.

FIG. 6 depicts a pattern of hydrophobic material printed onto a hydrophilic basesheet.

FIG. 16 is a table of physical property results for Examples 3–6.

FIG. 17 is a table of physical property results for Examples 7–10.

DETAILED DESCRIPTION OF THE DRAWINGS

Figure 1:
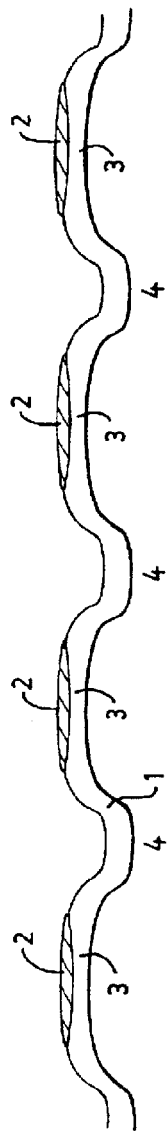
FIG. 1 is a cross-section of an absorbent web comprising a contoured, resilient basesheet having zones of hydrophobic material.

FIG. 1 shows a cross section of a contoured, inherently hydrophilic basesheet 1, preferably a resilient cellulosic tissue sheet, onto which hydrophobic material 2 has been deposited on the uppermost regions 3 of the contoured basesheet to form a composite absorbent web. The upper side of the web having the hydrophobic material 2 can serve as the skin-contacting layer of a topsheet or liner in an absorbent article. The hydrophobic material preferably resides only on the elevated regions of the basesheet as shown, preferably penetrating into no more than about 50% of the thickness of the basesheet, more specifically no more than about 20% of the thickness of the basesheet, and most preferably no more than about 10% of the thickness of the basesheet. For some products, it may be desirable that the hydrophobic material lie almost exclusively on the upper (outer) surface of the fibers on the upper surface of the basesheet, with very little penetration into the basesheet itself. The hydrophobic material deposits generally have a thickness that rises some distance above the underlying hydrophilic basesheet. In some embodiments, the distance above the underlying hydrophilic basesheet can be less than 3 mm, less than 0.5 mm, less than 0.1 mm, less than 0.05 mm, or between 0.05 and 0.5 mm. In some preferred embodiments, the thickness of the hydrophobic deposits relative to the local thickness of the hydrophilic basesheet can be less than 50%, alternatively less than about 20%, alternatively less than about 10%, or between about 5% and 25%.

Figure 2:
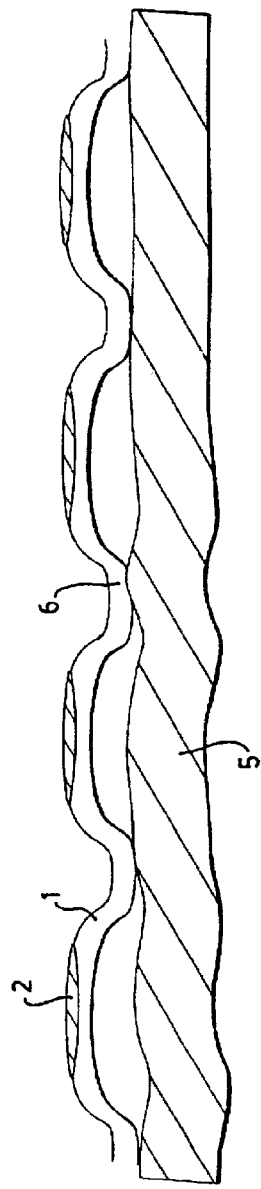
FIG. 2 depicts the absorbent web of FIG. 1 in contact with an underlying absorbent fibrous layer.

For best performance in terms of liquid absorption, the density of the basesheet preferably should be substantially uniform throughout any characteristic cross-section of the basesheet, as is characteristic of uncreped, through-air dried tissues and other paper sheets that have been dried by largely noncompressive means. Such a basesheet is relatively free of regions having low permeability and low absorbent capacity and tends to be more resilient when wet. The depressed regions 4 of the basesheet are substantially hydrophilic and can serve much as apertures do in an apertured film by providing pore space to receive liquids and by providing regions in the midst of hydrophobic material where liquid can be wicked into an absorbent medium, the medium being the hydrophilic basesheet itself and optionally an underlying absorbent core preferably in liquid communicating contact with the composite web. The underlying absorbent core is preferably a fibrous mat such as a mat of fluff pulp. One such embodiment is depicted in FIG. 2, where the inherently hydrophilic basesheet 1 is in direct contact with a fibrous mat 5. For enhanced transport of liquid out of the composite web into the fibrous mat, the fibrous mat 5 may be provided with a heterogeneous structure having high density regions with small pores to provide high capillary pressure to pull liquid out of the composite web, while still having a significant amount of low density regions to provide adequate pore space to hold large quantities of fluid and to provide high permeability regions. A heterogeneously densified fibrous mat 5 can have a relatively dense upper layer in contact with the basesheet 1, or it can have a pattern of densified regions imparted by embossing or other means, preferably with at least some of the densified regions in direct contact with the lower hydrophilic portions 4 of the basesheet 1.

Figure 3:
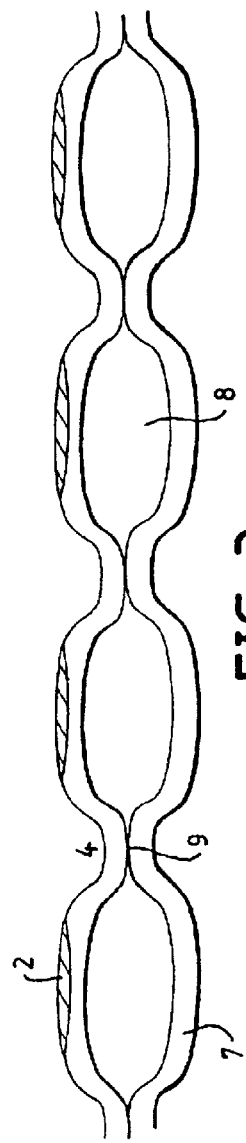
FIG. 3 depicts the absorbent web of FIG. 1 attached to an inverted basesheet having similar topography.

As shown in FIG. 3, the inherently hydrophilic basesheet 1 can also be in contact 9 with a web of similar topography having depressions 7 to form a multi-ply structure with significant interply pore space 8. Preferably, the web provides a combination of desired material properties: wet resiliency, to maintain shape and bulk when wet; absorbency and good capillary structure to provide rapid intake of fluid in the hydrophilic areas, softness on the upper surface on the body side for improved comfort; flexibility for comfort during use; and a three-dimensional contour to reduce contact area against the body, thus resulting in less of a wet feel when wet.

The inherently hydrophilic basesheet can be produced by a wide variety of 15 methods. Preferably, the basesheet, prior to any calendering that may be desired, is characterized by a low-density three-dimensional structure created in substantial part before the sheet reaches a solids level (dryness level) of about 60% or higher and preferably about 70% or higher. Suitable low-density three-dimensional structures can be achieved by a variety of means known in the arts of papermaking, tissue production, and nonwoven web production, including but not limited to the use of specially treated high-bulk fibers such as curled or chemically treated fibers as an additive in the furnish, including the fibers taught by C. C. Van Haaften in "Sanitary Napkin with Cross-linked Cellulosic Layer," U.S. Pat. No. 3,339,550, issued Sep. 5, 1967, which is hereby incorporated by reference; mechanical debonding means such as differential velocity ("rush") transfer between fabrics or wires, hereafter described; mechanical straining or "wet straining" of the moist web, including the methods taught by M. A. Hermans et al. in U.S. Pat. No. 5,492,598, "Method for Increasing the Internal Bulk of Throughdried Tissue," issued Feb. 20, 1996, herein incorporated by reference, and M. A. Hermans et al. in U.S. Pat. No. 5,411,636, "Method for Increasing the Internal Bulk of Wet-Pressed Tissue," issued May 2, 1995, herein incorporated by reference; molding of the fiber onto a three-dimensional wire or fabric, such as the fabrics disclosed by Chiu et al. in U.S. Pat. No. 5,429,686, "Apparatus for Making Soft Tissue Products," issued Jul. 4, 1995, which is hereby incorporated by reference, including differential velocity transfer onto or from said three-dimensional wire or fabric; wet embossing of the sheet; hydroentanglement of fibers; wet creping; and the optional use of chemical debonding agents. Inherently hydrophilic basesheets may also be produced from composites of synthetics and pulp fibers, with one embodiment disclosed in commonly owned U.S. Pat. No. 5,389,202, "Process for Making a High Pulp Content Nonwoven Composite Fabric," issued Feb. 14, 1995 to Cherie H. Everhart et al., hereby incorporated by reference.

Air laid mixtures of cellulosic and synthetic fibers are within the scope of the present invention. Pulp fibers for air laying may be prepared by comminution, as by a hammermill, or other means known in the art. Methods of forming air laid materials are well known in the art, including, for example, the methods disclosed by Dunning and Day in U.S. Pat. No. 3,976,734, issued Aug. 24, 1976, and U.S. Pat. No. 5,156,902, issued Oct. 20, 1992 to Pieper et al., both of which are herein incorporated by reference. Suitable papermaking fibers for air laying may include hardwood or softwood, low or high yield fibers, and chemically treated fibers such as mercerized pulps, chemically stiffened or crosslinked fibers, sulfonated fibers, and the like. Useful fiber preparation methods include those of Hermans et al. disclosed in U.S. Pat. No. 5,501,768, issued Mar. 26, 1996, and U.S. Pat. No. 5,348,620, issued Sep. 20, 1994, both of which are herein incorporated by reference. Fiber softening methods known in the art may also be employed, including the compounds disclosed by Smith et al. in U.S. Pat. No. 5,552,020, issued Sep. 3, 1996, herein incorporated by reference. The pulp fibers may be entrained in air or steam and combined or commingled with newly formed, hot synthetic fibers from a meltblown or spunbond process, or the pulp fibers may be mixed with a stream of relatively short, cut synthetic fibers (preferably less than 22 mm in length) entrained in air. Bonding agents and adhesives may be used to impart stability and wet strength to the air laid structure, or heat may be applied to partially melt some of the synthetic fibers to provide bonding. One embodiment comprises mixtures of papermaking fibers and meltblown polymers known as "coform" as taught in U.S. Pat. No. 4,100,324 issued to Anderson et al.; U.S. Pat. No. 4,879,170 issued to Radwanski et al.; and U.S. Pat. No. 4,931,355 issued to Radwanski et al., all herein incorporated by reference. For the purposes of this invention, steps should be taken to impart appropriate texture to the web. Such steps may include forming on a screen having a pattern of low and high permeabilities to produce a web of patterned basis weight and thickness, spot bonding, pattern bonding, embossing, pulling out regions of the web in the z-direction to disrupt the surface in a predetermined pattern, ultrasonic pattern bonding, web disruption with hydraulic jets of liquid, and so forth. Desirably, inherently hydrophobic synthetic fibers may be treated to increase wettability with respect to water, urine or menses, using methods such as surfactant coating, supercritical fluid deposition of surfactants or other surface active agents on the fiber surface, deposition of protein or amphiphilic protein, corona discharge treatment, ozonation, coating with hydrophilic matter, and the like. When synthetic fibers are used in the production of the basesheet, they may constitute 70% or less by weight of the basesheet, preferably 40% or less, more preferably 20% or less, more preferably still 10% or less, and most preferably between about 1% and about 10%. Alternatively, the web may comprise between about 1% and about 10% synthetic fibers. Alternatively, the web may comprise between about 1% and 50% of synthetic polymer fibers. A lower content of synthetic fiber is generally desirable to reduce cost, although other factors may be more important in determining the optimum fiber mix for a specific product. Other suitable materials for incorporation in absorbent articles of the present invention include the soft webs of Tanzer et al. in U.S. Pat. No. 5,562,645, issued Oct. 8, 1996, herein incorporated by reference.

In a preferred embodiment, the basesheet is a wet-laid tissue produced without creping and dried by non-compressive means. Techniques for producing such sheets are disclosed by S. J. Sudall and S. A. Engel in U.S. Pat. No. 5,399,412, "Uncreped Throughdried Towels and Wipers Having High Strength and Absorbency," issued Mar. 21, 1995; R. F. Cook and D. S. Westbrook in U.S. Pat. No. 5,048,589, "Non-creped Hand or Wiper Towel," issued Sep. 17, 1991; and J. S. Rugowski et al., "Papermaking Machine for Making Uncreped Throughdried Tissue Sheets," U.S. Pat. No. 5,591,309, Jan. 7, 1997; all herein incorporated by reference.

Figure 4:
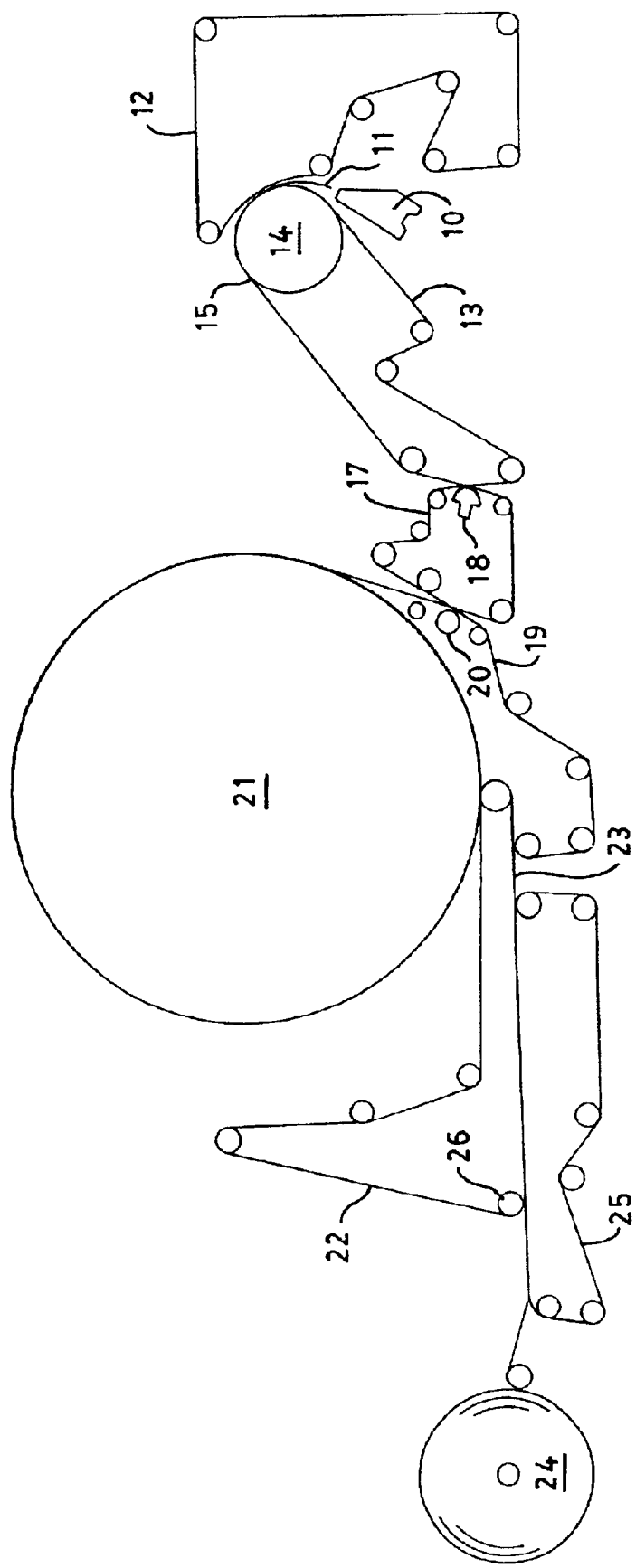
FIG. 4 depicts a paper machine suitable for producing the contoured, resilient basesheet of the present invention shown in FIG. 1.
Figure 7:
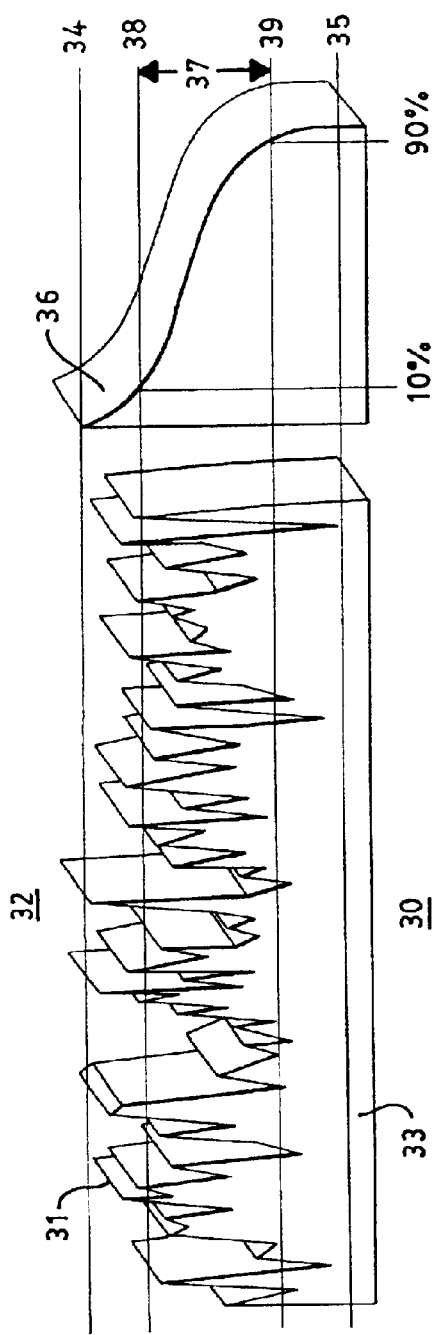
FIG. 7 depicts a height profile and several material lines to illustrate the definition of material surface curve and the P10 height.
Figure 8:
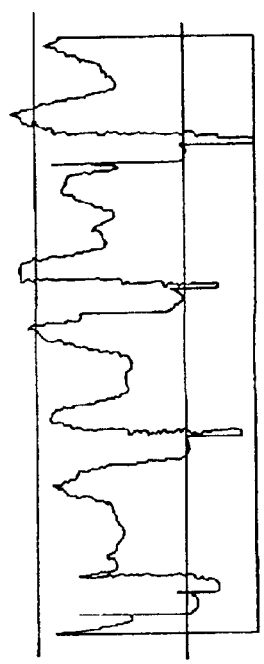
FIG. 8 depicts a CADEYES profile from Sample 13 of the present invention.
Figure 9:
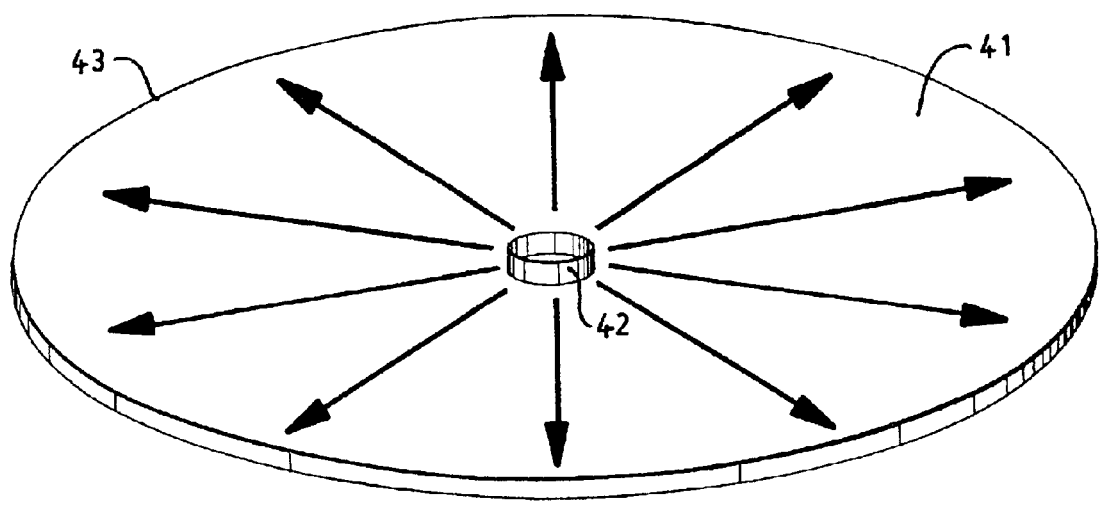
FIG. 9 portrays the flow pattern in a paper disk during an In-Plane Permeability measurement (angle view).
Figure 10:
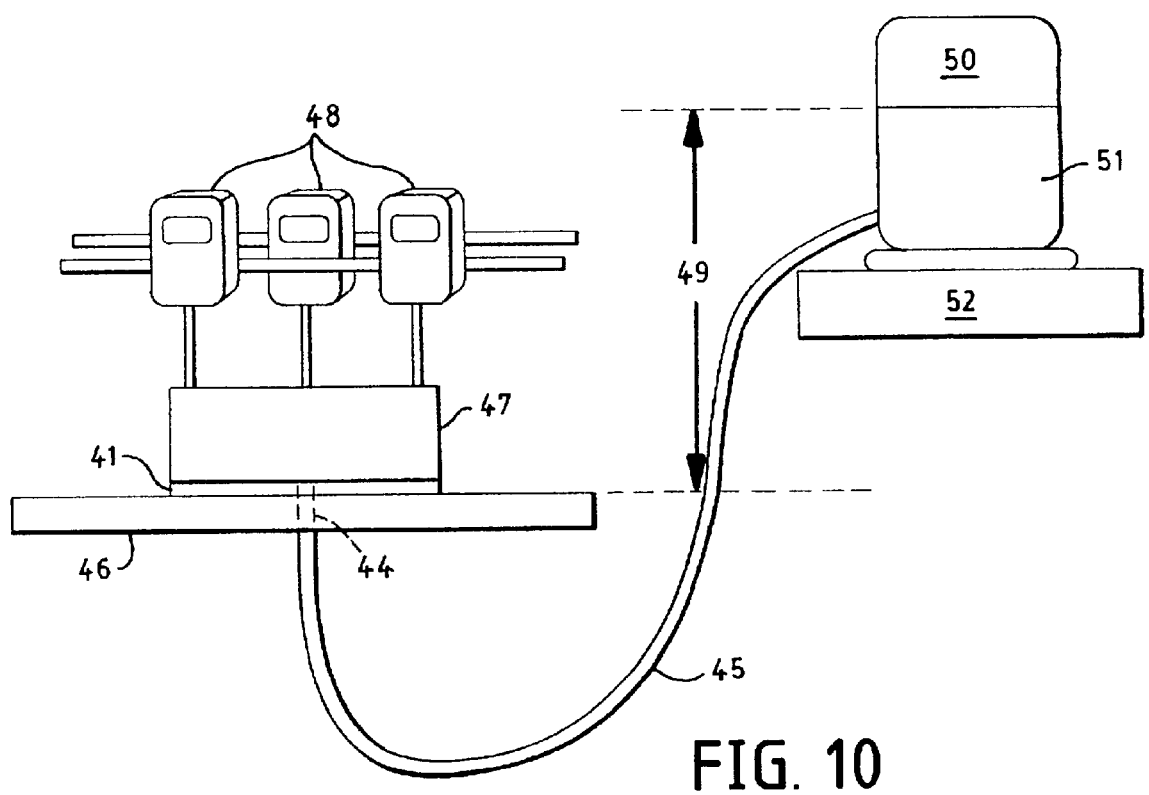
FIG. 10 is a side view of the In-Plane Permeability apparatus.
Figure 11:
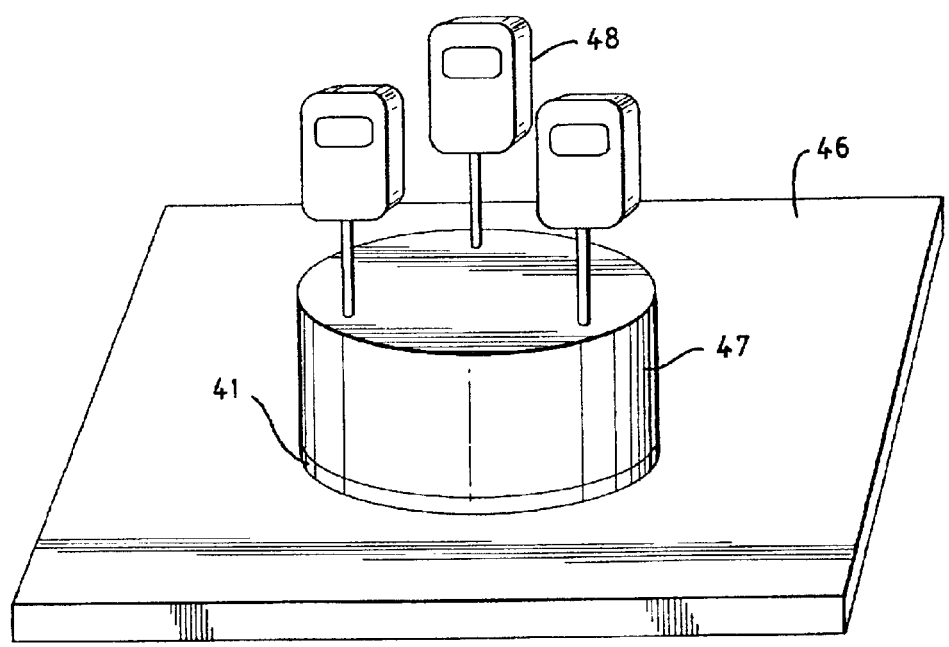
FIG. 11 is a top view of the brass platen and thickness gauges in the In-Plane Permeability apparatus.

A preferred method for producing the basesheet for the present invention is depicted in FIG. 4. For simplicity, the various tensioning rolls schematically used to define the several fabric runs are shown but not numbered. It will be appreciated that variations from the apparatus and method illustrated in FIG. 4 can be made without departing from the scope of the invention. Shown is a twin wire former having a layered papermaking headbox 10 which injects or deposits a stream 11 of an aqueous suspension of papermaking fibers onto the forming fabric 13 which serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric. The headbox 10 may be a conventional headbox or may be a stratified headbox capable of producing a multilayered unitary web. For example, it may be desirable to provide relatively short or straight fibers in one layer of the basesheet to give a layer with high capillary pressure, while the other layer comprises relatively longer, bulkier, or more curled fibers for high permeability and high absorbent capacity and high pore volume. It may also be desirable to apply different chemical agents to separate layers of a single web to optimize dry and wet strength, pore space, wetting angle, appearance, or other properties of a web. Multiple headboxes may also be used to create a layered structure, as is known in the art.

The wet web is transferred from the forming fabric to a transfer fabric 17 preferably traveling at a slower speed than the forming fabric in order to impart increased stretch into the web. This is commonly referred to as "rush" transfer. One useful means of performing rush transfer is taught in U.S. Pat. No. 5,667,636, issued Mar. 4, 1997 to S. A. Engel et al., herein incorporated by reference. The relative speed difference between the two fabrics can be from 0–80 percent, preferably greater than 10%, more preferably from about 10 to 60 percent, and most preferably from about 10 to 40 percent. Transfer is preferably carried out with the assistance of a vacuum shoe 18 such that the forming fabric and the transfer fabric simultaneously converge and diverge at the leading edge of the vacuum slot.

The web is then transferred from the transfer fabric to the throughdrying fabric 19 with the aid of a vacuum transfer roll 20 or a vacuum transfer shoe, optionally again using a fixed gap transfer as previously described. The throughdrying fabric can be traveling at about the same speed or a different speed relative to the transfer fabric. If desired, the throughdrying fabric can be run at a slower speed to further enhance stretch. Transfer is preferably carried out with vacuum assistance to ensure deformation of the sheet to conform to the throughdrying fabric, thus yielding desired bulk and appearance. Suitable throughdrying fabrics are described in U.S. Pat. No. 5,429,686 issued to Kai Chiu et al., previously incorporated by reference.

In a preferred embodiment, the fabric comprises a sculpture layer superposed on or integrally connected to a load bearing layer, said sculpture layer comprising elongated, raised elements having an aspect ratio of at least 4, preferably at least 6, more preferably at least 10, more preferably still at least 20, and most preferably between about 8 and about 50. The fabric may be woven or nonwoven. In one embodiment, the fabric is a woven fabric wherein the load bearing layer comprises interwoven machine-direction warps and cross-direction chutes and the sculpture layer comprises additional warps or chutes interwoven in the weave of the load bearing layer, wherein the highest knuckles of the sculpture layer may be higher than the highest knuckles of the load bearing layer by about 0.1 mm or greater, preferably 0.2 mm or greater, more preferably 0.5 mm or greater, and most preferably between about 0.4 mm and about 2 mm. For purposes of imparting improved cross-direction stretch of the basesheet, the elongated, raised elements of the sculpture layer should be preferentially oriented in the machine direction.

The number of elongated, raised elements per square inch of the fabric should be between about 5 and about 300, more preferably between about 10 and about 100. The resulting throughdried basesheet will have elevated regions preferably comprising between about 5 and about 300 protrusions per square inch having a height relative to the plane of the basesheet, as measured in the uncalendered state and uncreped state, of about 0.1 mm or greater, preferably 0.2 mm or greater, more preferably about 0.3 mm or greater, and most preferably from about 0.25 to about 0.6 mm. When the basesheet structure comprises a relatively planar portion with both protrusions and depressions departing therefrom, the relatively planar portion is taken as the plane of the basesheet. In some structures, a basesheet plane may not be well defined. In such cases, the protrusion height can be measured relative to the characteristic depth of the deepest depressions. In any case, the protrusion height relative to the characteristic depth of the deepest depressions, as measured in the uncalendered state and uncreped state, can be about 0.1 mm or greater, preferably 0.3 mm or greater, more preferably about 0.4 mm or greater, more preferably still about 0.5 mm or greater, and most preferably from about 0.4 to about 1.2 mm. In one specific embodiment, the elevated regions of the basesheet correspond to elevated machine-direction knuckles from a sculpture layer of a three-dimensional throughdrying fabric used to produce an uncreped throughdried web. Webs formed in this manner have unusually high values of cross-direction stretch prior to failure, as measured in standard tensile tests, of 6% or greater, preferably 9% or greater, and more preferably 12% or greater, due to the high cross-direction topography imparted by the elevated machine-direction elements on a throughdrying fabric. The machine direction stretch can be enhanced by rush transfer and can be at least as great as the cross-direction stretch and preferably at least 10% and more preferably at least 14%.

The level of vacuum used for the web transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the throughdrying fabric, the web is final dried to a consistency of about 94 percent or greater by the throughdryer 21 and thereafter transferred to a carrier fabric 22. The dried basesheet 23 is transported to the reel 24 using carrier fabric 22 and an optional carrier fabric 25. An optional pressurized turning roll 26 can be used to facilitate transfer of the web from carrier fabric 22 to fabric 25. Suitable carrier fabrics for this purpose are Albany International 84M or 94M and Asten 959 or 937, all of which are relatively smooth fabrics having a fine pattern. Although not shown, reel calendering or subsequent off-line calendering can be used to improve the smoothness and softness of the basesheet.

The basesheet may be slitted, perforated, or provided with apertures formed by cutting, stamping, or the piercing action of fine water jets. Such perforations or apertures may assist in the transfer of fluid into an underlying absorbent core. Preferably, the apertures are provided near or within depressed areas of the contoured basesheet that serve as hydrophilic zones. FIG. 5 depicts a cross-section of one such embodiment in which the basesheet 1 has been provided with perforations 27 in the low, hydrophilic regions.

Co-aperturing of the nonwoven material with the underlying basesheet, wherein the nonwoven web and the basesheet are simultaneously apertured as with pin aperturing of a two-layer structure, is possible within the scope of the present invention but is not preferred. Co-aperturing tends to place hydrophobic matter from the nonwoven web over the hydrophilic matter of the basesheet in the apertures, such that fluid entering the aperturing might encounter a hydrophobic barrier between it and the basesheet. It is desired that fluid entering the apertures be able to flow into the basesheet. Apertures in the basesheet may enhance subsequent transport into the underlying core, but the hydrophobic properties of the basesheet should contribute positively to the fluid handling performance of the composite cover material.

FIG. 7 to 11 have been previously discussed.

Figure 12:
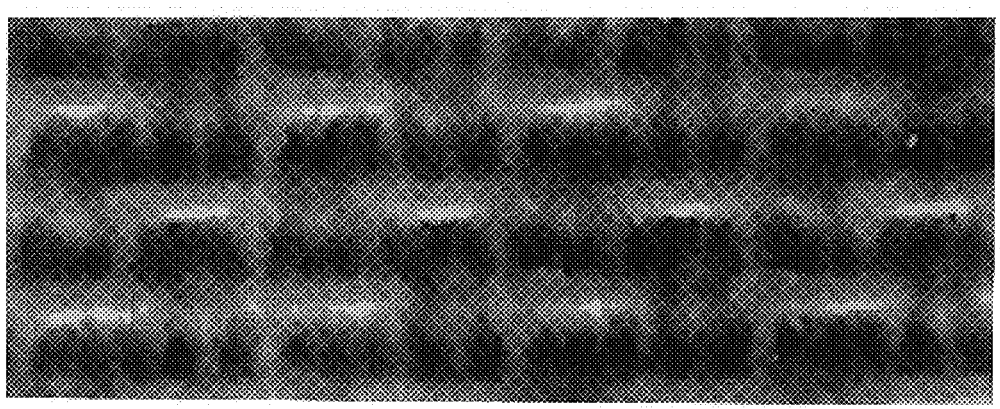
FIG. 12 depicts the grayscale height map of a section of uncreped tissue basesheet showing relatively high regions as light gray and lower regions as darker gray or black.

FIG. 12 shows a representative portion of a grayscale height map of a basesheet structure of potential value in the present invention, acquired by the CADEYES moiré interferometer (Medar, Inc. Farmington Hills, Mich.) having a 38-mm field of view. The tissue is an uncreped through-air dried structure having a surface depth of about 0.3 mm. Preferably, the basesheet is textured or molded prior to complete drying to impart an Overall Surface Depth in the dried structure of about 0.1 mm. or greater, more preferably about 0.3 mm. or greater, still more preferably about 0.4 mm. or greater, still more preferably about 0.5 mm. or greater, and most preferably from about 0.4 to about 0.8 mm. In another preferred embodiment, the basesheet further contains at least 10% by weight of high yield or other wet resilient pulp fibers and an effective amount of wet strength resin such that the wet:dry tensile ratio is at least about 0.1. The uppermost, elevated regions of the basesheet preferably offer relatively smooth and flat plateaus in order to be placed against skin with relatively little sense of grittiness or abrasion.

The hydrophobic material 2 on the basesheet as shown in FIG. 1 is preferably deposited on relatively elevated regions of the web, such as the light gray or white regions on the height map of FIG. 12, in order to place hydrophobic regions in contact with the user's body when the web is used as a topsheet in an absorbent article. The hydrophobic material is preferably deposited over a large enough portion of the basesheet to render a distinct improvement in dry feel while still allowing liquid transport by wicking in the z-direction (thickness direction, normal to the plane of the web) in multiple hydrophilic regions. The proper application of hydrophobic matter to a fraction of the upper surface of the hydrophilic basesheet will generally result in a decrease of Rewet value relative to the untreated basesheet (meaning an improvement in the dry feel) of at least about 10%, more specifically at least about 20%, more specifically at least about 30%, still more specifically at least about 40%, and most specifically from about 10% to about 60%. The resulting Rewet value is preferably less than about 1 g, more specifically less than about 0.65 g, more specifically less than about 0.5 g, still more specifically less than about 0.4 g, and most specifically less than about 0.3 g. The resulting Normalized Rewet value is preferably less than about 1, more specifically less than about 0.7, more specifically less than about 0.5, still more specifically less than about 0.4, and most specifically less than about 0.3. In one embodiment, there is essentially no hydrophobic matter present below the 50% material line of a characteristic profile of the web, or below the midplane of a typical cross section of contoured web.

In one embodiment, the hydrophobic matter is applied in a manner designed to limit lateral (in-plane) wicking of liquids to prevent seepage or leakage from the edges of an absorbent article while also improving the dry feel. Producing this embodiment normally requires that hydrophobic material or materials be added to the upper surface of the hydrophilic basesheet in two ways such that some of the hydrophobic matter penetrates substantially into the basesheet to establish a barrier region to inhibit in-plane wicking, while the remainder of the hydrophobic matter is applied more lightly to avoid substantial penetration into the basesheet. The barrier regions may also use hydrophobic matter to fill in the depressions of the web to prevent flow of liquid along surface channels or pores. Different hydrophobic materials and application means may be used for the two or more regions of differing penetration depth or differing basis weight of application. One approach suitable for use in absorbent articles such as feminine pads or incontinence pads is to apply longitudinal bands of a hydrophobic material in liquid form, such as a melted wax or polymeric compound, applied heavily enough to permeate into the basesheet for a significant portion of the thickness of the basesheet, with said bands being near the edges of the absorbent article to limit seepage from the edge. The remaining portion of the basesheet may be treated with hydrophobic matter applied more superficially to be less penetrating.

Suitable hydrophobic materials may comprise compounds which are solid or highly viscous at room temperature but become liquid or significantly less viscous at elevated temperature, enabling application of the liquid at elevated temperature by gravure printing, spray, brush application, or other means, whereupon the liquid solidifies, gels, or becomes substantially immobile at room temperature or body temperature. The hydrophobic agent may also be dissolved, dispersed, or emulsified in a liquid carrier, such as water, and applied to the web by means such as coating, spraying, or printing, whereafter part of the liquid carrier is removed by evaporation, sorption, or other means to leave a hydrophobic coating or impregnation on the web. The hydrophobic agent may also comprise solid particles such as PTFE, polyolefins, or other polymers that have been ground and formulated into a viscous grease or paste. Additionally, the hydrophobic matter may be in solid form, such as fibers or particles that are attached adhesively to the basesheet or attached by entanglement, hydroentanglement, electrostatic attraction, and so forth.

Suitable hydrophobic materials include silicone compounds, fluorocarbons, PTFE, waxes, wax emulsions, polyurethane emulsions, fats and fatty acid derivatives, polyolefins, nylon, polyesters, glycerides, and the like, as well as mixtures of the same. Several suitable materials containing solidified mixtures of waxes and oils are disclosed in commonly owned U.S. Pat. No. 5,601,871, "Soft Treated Uncreped Throughdried Tissue," issued Feb. 11, 1997 to D. Krzysik et al., herein incorporated by reference. Disclosed therein are compounds containing oil, wax, and optionally fatty alcohols, said compositions having melting points between about 30° C. to about 70° C. When distributed relatively uniformly over an uncreped tissue, said compositions significantly reduce liquid intake rates and reduce friction against the skin. It is believed that the hydrophobic compositions disclosed by Krzysik et al. could also be used advantageously in the present invention through a macroscopically nonuniform application of said compositions to a portion of the most elevated regions of a three-dimensional, resilient, hydrophilic basesheet in such a manner as to avoid significant reduction of liquid intake rates.

As disclosed by Krzysik et al., suitable oils include, but are not limited to, the following classes of oils: petroleum or mineral oils, such as mineral oil and petrolatum; animal oils, such as mink oil and lanolin oil; plant oils, such as aloe extract, sunflower oil, and avocado oil; and silicone oils, such as dimethicone and alkylmethyl silicones. Suitable waxes include, but are not limited to the following classes: natural waxes, such as beeswax and carnauba wax; petroleum waxes, such as paraffin and ceresine wax; silicone waxes, such as alkyl methyl siloxanes; or synthetic waxes, such as synthetic beeswax and synthetic sperm wax. Useful silicone compounds and methods of application are known in the art, including those of Kasprzak in U.S. Pat. No. 5,302,382, issued Apr. 12, 1994, and Kaun in U.S. Pat. No. 5,591,306, issued Jan. 7, 1997, both of which are herein incorporated by reference.

The amount of fatty alcohol, if present, in the compositions of Krzysik et al. can include those having a carbon chain length of $C_{14}$–$C_{30}$, including cetyl alcohol, stearyl alcohol, behenyl alcohol, and dodecyl alcohol.

For some embodiments of the present invention, it is desired that the hydrophobic material have a melting point well above typical body temperatures since absorbent articles containing the web of the present invention may be worn against the body under hot conditions, and any melting of the hydrophobic material may interfere with the performance of the absorbent article and eliminate the advantage of a dry feel. For such articles containing the compositions of Krzysik et al. and other compositions, said compositions should have a melting point above about 35° C., specifically above 40° C., more specifically above about 45° C., and more specifically still above 50° C.

Other suitable hydrophobic compositions comprise up to 30 weight percent oil and from about 50 to about 100 weight percent wax, said compositions having a melting point of from about 40° C. to about 200° C., more specifically from 70° C. to about 160° C., more specifically above 75° C., and more specifically still from about 85° C. to 140° C. For purposes herein, "melting point" is the temperature at which the majority of the melting occurs, it being recognized that melting actually occurs over a range of temperatures. Hydrophobic materials may also be used which do not melt or which degrade or decompose prior to or during melting.

Examples of water repellent agents which are potentially useful in the present invention include polyurethane emulsions such as Aerotex 96B of American Cyanamid; fluorochemical agents such as FC 838, FC 826, and the SCOTCHGARD compounds sold by Minnesota Mining and Manufacturing and Milease F-14 and Milease F-31X, sold by ICI. Also desirable are high molecular weight cationic fluorocarbons which can be formed into aqueous emulsions for ease of application and handling. An example of a potentially useful wax emulsion is Phobotex, sold by Ciba. A variety of other water-repellent materials that can be applied to paper webs are reviewed and disclosed in U.S. Pat. No. 5,491,190, issued Feb. 13, 1996 to Paul E. Sandvick and Calvin J. Verbrugge, incorporated herein by reference. Sandvick and Verbrugge focus primarily on the use of mixtures of fatty acids and polymers for repulpable paper sheets. Various wax and polymer compositions of potential value for the present invention are disclosed in U.S. Pat. No. 3,629,171 to Kremer et al.; U.S. Pat. No. 3,417,040 to Kremer; U.S. Pat. No. 3,287,149 to Dooley et al.; U.S. Pat. No. 3,165,485 to Ilnyckyj et al.; and U.S. Pat. No. 2,391,621 to Powell, et al., all of which are herein incorporated by reference. Mixtures of hydrophobic latex and wax may also be used, including those taught in U.S. Pat. No. 4,117,199 to Gotoh et al., herein incorporated by reference. British Pat. No. 1,593,331 to Vase teaches a method for treating paper and paperboard to make them water resistant by coating them with an aqueous latex coating composition. The latex coating composition is an acrylic polymer and a metal stearate or wax where the wax is at least 20% by weight of the total acrylic polymer and metal stearate present. The metal stearate is preferably calcium stearate. Latex emulsions, latex foams, and water absorbing polymers may be used, including those disclosed in U.S. Pat. No. 5,011,864, issued Apr. 30, 1991 to Nielsen and Kim, herein incorporated by reference, which also discloses combinations containing chitosan. Potentially useful latexes also include those disclosed by Stanislawczyk in U.S. Pat. No. 4,929,495, and the anionic latex compounds are disclosed in U.S. Pat. No. 4,445,970, issued May 1, 1984, both of which are herein incorporated by reference. After application, the coating is dried or cured on the paper. For the present invention, the composition would be applied nonuniformly to the upper surface of a basesheet.

Other examples of aqueous emulsions and emulsifiable compositions for coating paper and the like are found in U.S. Pat. No. 3,020,178 to Sweeney et al. and U.S. Pat. No. 3,520,842 to Crean (aqueous mixtures of petroleum wax, a polymeric olefin material and a fatty acid are added to water containing an amine soap-forming agent such as an alkanolamine, followed by agitation and homogenization to form an aqueous emulsion coating composition). The hydrophobic matter may also comprise formulations intended to promote skin wellness and comfort. For example, the hydrophobic matter may include a hydrophobic base such as mineral oil, waxes, petrolatum, cocoa butter, and the like, combined with effective amounts of skin wellness additives or pharmaceutical agents such as antibiotics and or anti-bacterial agents, anti-fungal agents, Vitamin E (alpha tocopherol), lanolin, silicone compounds suitable for skin care, cortisone, zinc oxide, baking soda, corn silk derivatives, avocado oil, emu oil, other natural plant and animal oils, and the like.

Hydrophobic material may also be applied in fibrous or particulate form and attached to the basesheet through thermal fusion, chemical binding through the use of a binder agent or adhesive, preferably a water-repellent binder, entanglement (resulting from high velocity impact against a porous web), electrostatic attachment, and the like. In a preferred embodiment, the hydrophobic material, whether applied as fibers, as particles, or as a liquid or slurry, may be contiguously deposited to form an interconnected network, such as the network of lines shown in FIG. 6, in which case the hydrophilic regions are isolated from one another. In addition to materials previously described, useful particulate hydrophobic agents include talcum powder and lycopodium powder.

Preferably, the hydrophobic material is applied to the desired regions with an area-averaged local dry basis weight in the range of from about 0.5 to about 50 gsm, more specifically in the range of from about 1 to about 10 gsm, more specifically about 5 gsm or less, and most specifically about 3 gsm or less. The hydrophobic matter preferably comprises about 30% or less of the total mass of the dry absorbent web, more specifically about 20% or less, more specifically about 10% or less, and most specifically from about 1% to about 15% of the total mass of the dry absorbent web. The basis weight of the underlying basesheet can be from about 10 to about 200 gsm, more specifically from about 15 to about 70 gsm, and most specifically from about 15 to about 40 gsm. For multi-ply tissue structures, it is preferred that the basis weight be less than about 40 gsm and more specifically less than about 30 gsm.

In addition to hydrophobic matter, other agents may be suitably added to the basesheet in accordance with this invention, including superabsorbent particles or fibers. Superabsorbent material may be deposited or attached in the depressed regions of the upper surface of the basesheet, or preferably may be incorporated within the fibrous structure of the basesheet, attached to the lower surface of the basesheet, or incorporated between the basesheet and an attached absorbent core. Other chemical agents may be added to either surface or both surfaces, or dispersed throughout the basesheet, applied to inner or outer layers of the basesheet, or applied to selected surface regions of the basesheet, including application in a regular pattern as by gravure printing. Such chemical agents include emollients, lotions, chemical softeners, opacifiers, optical brighteners, wet strength agents, quaternary ammonium salts, proteins, crosslinking agents, virucides, bactericides, perfumes, dyes, chemical debonders, plasticizers for high yield fibers, zeolites or other agents for odor control, and the like. Chitosan and related derivatives may be incorporated in the articles of the present invention for their anti-bacterial or other health benefits; triclosan and other anti-bacterial agents may likewise be incorporated.

Various mechanical and physical treatments may be applied to the basesheet before or after addition of hydrophobic material to improve the mechanical properties, softness, or functionality of the web. Such treatments include brushing, differential velocity transfer between belts or fabrics, penetration by high velocity air jets, needling, hydroentanglement, calendering, soft nip calendering, thermal gradient calendering, corona discharge treatment, electret formation, microstraining, dry creping, embossing, slitting, and aperturing. Preferably, the basesheet is not co-apertured with the topsheet.

Also within the scope of the present invention are absorbent webs in which both sides of the web have been treated with hydrophobic material. Such an embodiment may be useful for absorbent towels and other materials where absorption may occur on either surface. In that case, it is preferred that hydrophobic material be placed on the most elevated regions of both surfaces, the elevated regions being the highest regions when the respective surface is facing up. Since the depressions on the upper surface will generally correspond to elevated regions on the lower surface when the lower surface is facing up, especially when the web has substantially uniform thickness throughout its cross section, the hydrophobic material on one surface will generally not be superposed directly over other hydrophobic material on the other surface but the hydrophobic regions on the two surfaces will tend to be in a staggered relationship to each other. The type of hydrophobic material, its method of application, and the amount applied may differ on both sides. Likewise, multiple applications of different hydrophobic materials may be performed on a single surface to achieve desired properties or a desired visual appearance, including the use of mutlicolored fiber patches, colored adhesives, and the like.

The scope of the present invention also includes multi-ply basesheet structures and laminates with one or more layers being the dual-zoned absorbent webs described above. For example, the traditional fluff pulp absorbent core used in many absorbent articles may be replaced by a series of resilient basesheet layers, such as the wet resilient uncreped, through-air dried basesheets described in Examples 7–10 below, and a dual-zoned absorbent web containing hydrophobic material could be placed in superposed relation on said series of resilient basesheet layers. All or some of the multiple plies may be further provided with apertures, slits, embossments, and the like. Multiple plies may be fixedly attached to each other through adhesives, sewn thread, entanglement by needling or fluid jets, embossing, and the like.

An excellent hand towel can be made by taking advantage of the unusually high wet resiliency of uncreped, non-compressively dried basesheets, especially those containing resilient fibers such as high-yield fibers and containing wet strength agents. The fiber-fiber bonds of such sheets comprise hydrogen and covalent bonds which are formed during non-compressive drying while the sheet is in a molded, three-dimensional structure. While calendering may flatten such a basesheet, many of the bonds are undisturbed. When the basesheet is later wetted, the swelling fibers can be relieved of the stresses imparted by calendering and can return to the structure achieved during drying. In a sense, the bonds have locked in a memory of the basesheet structure achieved during drying and curing of wet strength resins. Thus it is possible to prepare a calendered, flat basesheet which can return to a bulkier, three-dimensional state upon wetting, as disclosed in commonly owned copending application Ser. No. 60/013,308 filed Mar. 8, 1996 to D. Hollenberg et al., herein incorporated by reference. Such a "thin when dry, thick when wet" material can be used advantageously in the present invention. By adding hydrophobic material to the elevated regions of a basesheet and then calendering the basesheet, or alternatively, by adding hydrophobic material to the previously-high spots after calendering, a relatively thin, flat absorbent web is produced which has hydrophilic and hydrophobic regions in essentially the same plane. That structure can absorb fluids well upon contact because hydrophilic regions are in contact with the fluid. However, after wetting, the absorbent web expands such that the wet-feeling, hydrophilic regions are no longer in direct contact with the skin while the dry-feeling, hydrophobic regions become elevated to contact the skin. Such an absorbent web desirably has an Overall Surface Depth of about 0.2 mm or less while dry and about 0.3 mm or greater when wetted to a moisture content of 100%. Alternatively, the calendered absorbent web can have an Overall Surface Depth of about 0.3 mm or less while dry and about 0.4 mm or greater, more specifically about 0.5 mm or greater, when wetted to a moisture content of 100%.

Embodiments with Hydrophobic Fibers

Figure 13:
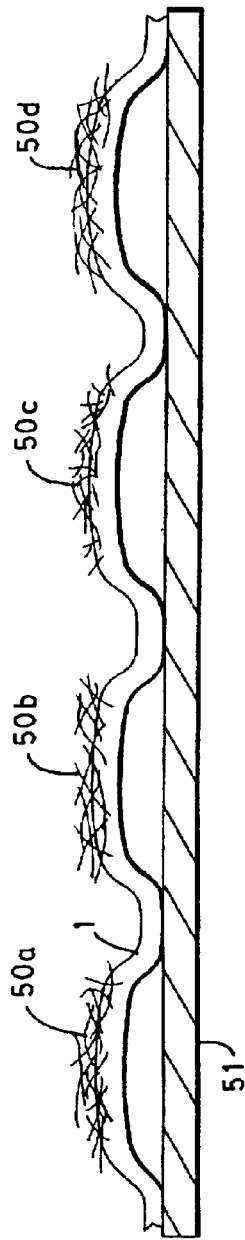
FIG. 13 is a cross-sectional view of an embodiment of this invention wherein the hydrophobic material comprises groups or tufts of hydrophobic fibers.

FIG. 13, depicts a form of a preferred set of embodiments wherein the hydrophobic material comprises groups or tufts of thin polyolefin fibers 50 or other hydrophobic fibers in order to provide a soft, clothlike feel. The fibers may comprise a variety of fiber lengths and types 50a and 50b, or may be primarily short fibers 50c with a fiber length smaller than the characteristic length of the elevated regions of the basesheet or may be primarily long fibers 50c with a length near or greater than the characteristic length of the elevated regions of the basesheet. In one embodiment, the tufts may be patches of short synthetic fibers attached preferentially to the elevated regions of the upper surface of the basesheet such that less than 80%, preferably less than 50%, and more preferably less than about 25% of the surface area of said basesheet is covered by the attached synthetic fibers. Such fibers may be applied by adhesives, thermal bonding, ultrasonic binding, electrostatic attraction, needling, entanglement, hydroentanglement or through the use of adhesives or binders, including water-repellent binders. The adhesives or binders may include hydrophilic agents such as polyvinyl alcohol, starch, cationic latexes, proteins, and the like, provided that the hydrophobic effect of the adhered fibers is not destroyed or severely reduced by the use of such adhesives. To ensure hydrophobic activity, water-repellent binders may be desirable, including materials such as polybutyl acrylate, styrene-acrylic copolymer, acrylic vinyl chloride copolymer, ethylene-acrylic acid copolymer, ethylene-vinyl acetate copolymer, ethylene-vinyl chloride copolymer, acrylic copolymer latex, styrene-butadiene latex, and vinyl chloride latex. Suitable repellent binders which may be utilized are Geon 580X83 and Geon 580X119, sold by Goodrich (consisting of vinylchloride latex); Emulsion E1497, and Emulsion E1847, sold by Rohm & Haas (consisting of an acrylic emulsion); and Rhoplex NW-1285, sold by Rohm & Haas (consisting of an acrylic emulsion); Airflex 120 and Airflex EVLC 453, sold by Air Products (consisting of ethylene vinyl chloride emulsions); Nacrylic 78-3990, sold by National Starch (consisting of an acrylic emulsion) and Primacor, sold by Dow Chemical (consisting of an ethylene/acrylic acid copolymer).

As shown in FIG. 13, a densified absorbent material 51 preferably is in contact with the lower side of the hydrophilic basesheet 1 wherein the densified absorbent material has a pore size smaller than the characteristic pore size of the basesheet 1 or a density greater than the density of the basesheet 1 and preferably has a density of about 0.1 g/cc or less, and more preferably about 0.2 g/cc or less. The densified absorbent material can be an airlaid web or a densified fluff pulp layer or other layers of cellulosic tissue. Preferably the densified absorbent material is stabilized to prevent excessive expansion or loss of absorbent capacity upon wetting. Stabilization can be achieved through the addition of thermosetting fibers or particles followed by heat treatment, by the addition of crosslinking agents followed by proper curing or heat treatment, by the addition of adhesives in the web, or other means known in the art. When fluid enters the basesheet 1, capillary forces can then wick the fluid into the absorbent material. If the material is stabilized, it will be less likely to lose its capillarity upon wetting but can continue to wick and retain fluids effectively.

The hydrophobic fibers 50 may be applied in isolated or interconnected patches along the uppermost surfaces of the hydrophilic basesheet, or, in the case of a relatively flat basesheet, they may be applied in a specific pattern to provide either isolated or interconnected patches of such material, or a combination of isolated and interconnected regions, preferably elevated relative to the surrounding untreated basesheet such that skin adjacent to the cover material will preferentially contact and sense the soft hydrophobic regions. Preferably, the fibers have a denier less than about 9, more specifically less than about 6, more specifically less than about 5, and most specifically from about 1 to about 5. Suitable polymers include ethylene/propylene copolymers, polyester copolymers, low-density polyethylene, acrylic, ethylene/vinyl acetate copolymer, polyethylene, polypropylene, chlorinated polyethylene, polyvinyl chloride, polyamide, high density polyethylene, linear low-density polyethylene, and the like. Conjugate fibers such as bicomponent sheath/core or bicomponent side-by-side fibers may also be used. Bicomponent fibers with a relatively low melting point material and a higher melting point material in a single fiber may be used by heating the fibers in contact with the basesheet such that the low melting point material melts and adheres the unmelted higher melting point material to the basesheet. Although continuous filaments of fibers may be employed, the preferred fibers have lengths of from about 0.3 mm to about 10 mm, more specifically from about 0.5 mm to about 5 mm, more specifically less than about 3 mm, and most specifically less than about 2 mm. Preferably the attached fibers have at least one end which is free and can deform or deflect under shear to provide a soft, velvety feel. The fibers should be fixedly attached such that they do not readily fall off or slough off excessively in use. The attached fibers may be applied to form a layer approximately one fiber diameter in depth or a layer having a plurality of fiber diameters in thickness, including 2 to 100 fiber diameters, more specifically 3 to 50 fiber diameters or more specifically still 3 to 10 fiber diameters in depth.

The fibers may part of a preformed nonwoven web or may be loose fibers deposited through air laying and subsequent bonding, preferably using a patterned vacuum surface to apply the fibers in a desired pattern, or else by applying a fairly uniform mat of short fibers onto the surface of the basesheet and bonding only the fibers on the uppermost regions of the surface of the basesheet. The latter process may include a heated nip in which the raised regions on the basesheet force better contact between the deposited fibers and a textured heated surface, such that fibers become thermally bonded to the web only at the highest points on the basesheet. The high spots on the textured heating surface or heating roll provide spot welding of the fibers onto the basesheet.

A useful method of attaching hydrophilic fibers requires first printing or depositing binder material or adhesive onto the uppermost regions of a textured basesheet, such as by gravure printing, followed by exposure of the basesheet to loose fibers entrained in air, as in an air laying process, such that the fibers are retained by the binder material on the printed regions but not retained elsewhere on the basesheet. Unadhered fibers could then be removed by blowing of air or by vacuum, and then recycled. In this manner thin mats of loose, fluffy fibers could be deposited and attached on the desired locations on the basesheet, preferably with minimal sheet penetration by the adhesive.

Fibers may be formed directly on the basesheet or deposited immediately after formation using melt blown or spun bond processes, adapted to provide fibers only in desired regions. Alternatively, a continuous thin, soft, bulky layer of a preformed melt blown or spun bond fibers may be cut to have apertures over the low regions of the tissue web and then positioned properly on the web and attached by thermal bonding or other means. In another embodiment, the fibers may be incorporated into a dilute aqueous slurry and applied onto the basesheet. This may be done during the formation of the basesheet itself with a layered headbox, resulting in a unitary basesheet containing a portion of soft, hydrophobic fibers embedded in the upper layer of an otherwise cellulosic basesheet. Additional application of water-repellent agents at the uppermost regions of the contoured surface of the basesheet may then be needed to ensure that said uppermost regions are sufficiently hydrophobic.

Figure 14:
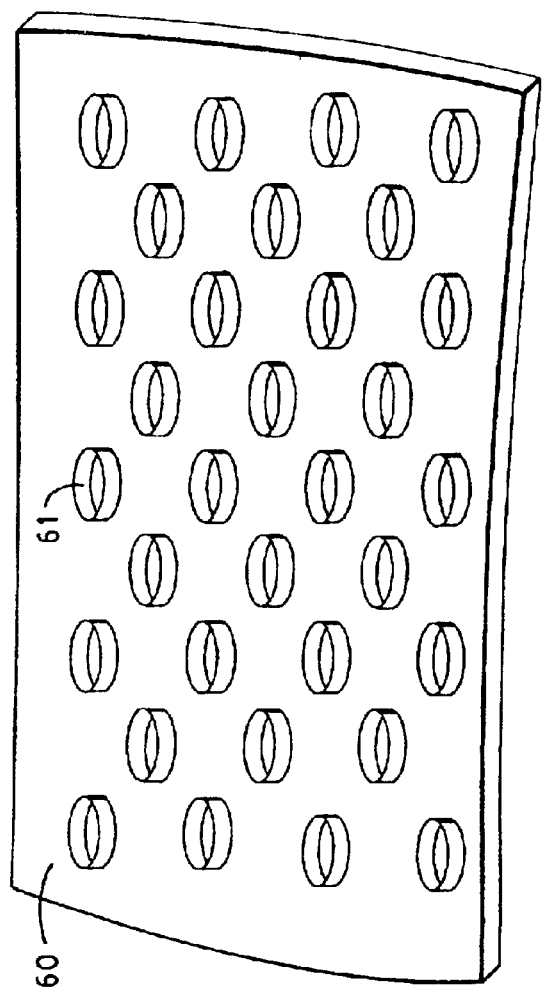
FIG. 14 is a perspective view of an apertured nonwoven web of hydrophobic fibers useful for purposes of this invention.

Applicants have found that a contiguous web of hydrophobic fibers, such as spunbond or meltblown nonwoven web of synthetic fibers, can be especially advantageous for use as the hydrophobic matter of the present invention, offering economical processing and excellent comfort. For effective removal of menses, mucous, runny bowel movement, and other viscous fluids, the nonwoven web should be provided with macroscopic apertures, slits, or other openings as shown in FIG. 14 to provide good access to the hydrophilic basesheet for body exudates. The openings or apertures 61 in the nonwoven web 60 should overlay a portion of the depressed regions in the hydrophilic basesheet such that fluid is repelled by the most elevated portions of the surface contacting the skin and drawn toward depressed regions that are not in direct contact with the skin.

Openings in a nonwoven web can be provided through pin aperturing; perf embossing and mechanical stretching of the web; die punching or stamping; hydroentangling to impart apertures by rearrangement of the fibers; water knives that cut out desired apertures or holes in the web; laser cutters that cut out portions of the web; patterned forming techniques, such as air laying of synthetic fibers on a patterned substrate to impart macroscopic openings, as disclosed by F. J. Evans in U.S. Pat. No. 3,485,706, issued Dec. 23, 1969, and U.S. Pat. No. 3,494,821, issued Feb. 10, 1970, both incorporated herein by reference; needle punching with sets of barbed needles to engage and displace fibers; and other methods known in the art. Pin aperturing of nonwoven materials is described in commonly owned U.S. Pat. No. 5,188,625, issued Feb. 23, 1993 to Van Iten, et al., herein incorporated by reference.

Openings or apertures can be created in a way that permits excellent registration of apertures 61 with the depressed regions of a three-dimensional through-dried tissue web. A modified form of hydroentangling may be especially useful in this regard. Such a process comprises placement of a nonwoven web 60 on the same type of through-drying fabric that is used to mold the associated basesheet during through drying. With the nonwoven web on the through-drying fabric, hydroentangling can be applied to drive fibers away from the elevated portions of the through-drying fabric, which will typically correspond to the depressed regions of the fabric-side of the through-air dried sheet. If the tissue web is to be used with the air-side toward the body in the absorbent article, then the nonwoven web should be placed on the backside of the through-drying fabric and then hydroentangled, for the elevated portions of the backside of the through-drying fabric will generally correspond to the depressed regions of the other side on which the tissue web is molded.

After hydroentangling on a through-drying fabric has provided the nonwoven web 60 with a pattern of apertures 61, the web can be registered with the through-dried tissue to put the apertures over the depressed regions to result in effective intake into the hydrophilic depressions while maintaining hydrophobic material on the elevated portions of the basesheet. Registration can be achieved with photoeyes and image analysis software or other mechanical means known in the art to control the position of the nonwoven web as it is placed on the molded basesheet by automated equipment.

Preferably, the openings are provided in a regular pattern over at least a portion of the topsheet of the absorbent article.

Figure 18:
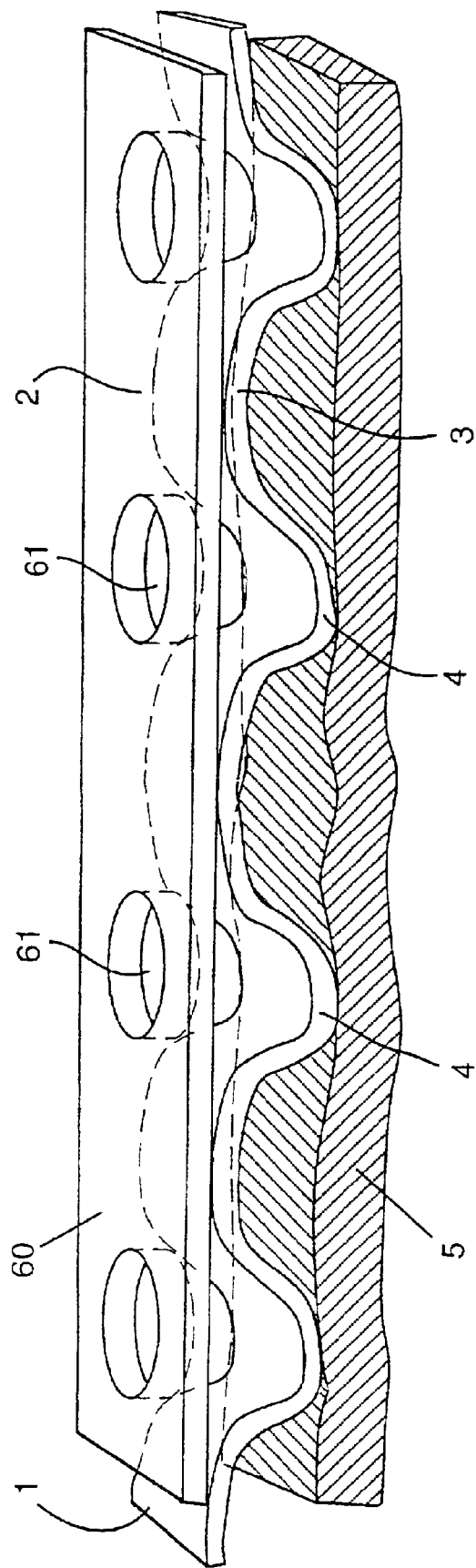
FIG. 18 depicts an apertured hyudrophobic web superposed over a basesheet according to the present invention.

FIG. 18 depicts a perspective view of a fibrous nonwoven web 60 comprising apertures 61, as in FIG. 14, except that the apertured web 60 is now shown joined to a textured basesheet 1 and the assembly is in contact with an underlying absorbent core 5. Apertures 61 in the nonwoven web 60 are substantially aligned with the depressed regions 4 of the basesheet 1. The nonwoven web 60 serves as a hydrophobic matter 2 on the most elevated portions 3 of the basesheet 1.

Figure 19:
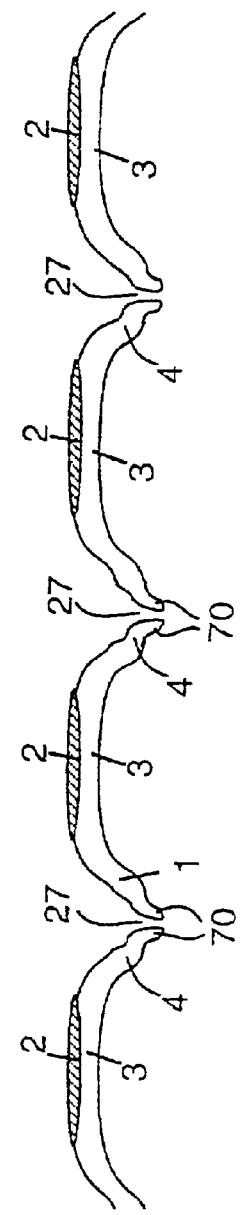
FIG. 19 depicts an apertured basesheet having protrusions about the apertures, the basesheet further comprising hydrophobic matter on the most elevated portions of the basesheet.

FIG. 19 depicts a cross-sectional view of an apertured basesheet 1 similar to that of the basesheet 1 of FIG. 5 except that the perforations 27 (apertures in the basesheet) have been formed in a manner that creates protrusions 70 extending from the lower portion of the basesheet and surrounding the apertures 70. The protrusions 70 can be wet resilient if formed in a moist state and dried.

Wicking of fluids into the apertures toward the hydrophilic basesheet can be enhanced by modification of the surface chemistry of the hydrophobic nonwoven web in the area of the apertures, such as by addition of surfactants to the nonwoven web in the vicinity of apertures or oxidation of fibers by plasma or other treatment. Alternatively, cellulosic fibers or other hydrophilic matter could be added to the region of the apertures to enhance wicking. For example, cellulosic fibers could be added to the periphery of the apertures to enhance wicking.

EXAMPLES

Example 1

To demonstrate an example of a textured, wet resilient absorbent web with improved dry feel, a suitable basesheet was prepared and modified by addition of hydrophobic material in the form of paraffin. The basesheet was produced on a continuous tissue making machine adapted for uncreped through-air drying, similar to the machine configuration shown in FIG. 4. The machine comprises a Fourdrinier forming section, a transfer section, a through-drying section, a subsequent transfer section and a reel. A dilute aqueous slurry at approximately 1% consistency was prepared from 100% spruce bleached chemithermomechanical pulp (BCTMP), pulped for 20 minutes at about 4% consistency prior to dilution. The spruce BCTMP is commercially available as Tembec 525/80, produced by Tembec Corp. of Temiscaming, Quebec, Canada. Kymene 557LX wet strength agent, manufactured by Hercules, Inc., Wilmington, Del., was added to the aqueous slurry at a dosage of about 20 pounds of Kymene per ton of dry fiber. The slurry was then deposited on a fine forming fabric and dewatered by vacuum boxes to form a web with a consistency of about 12%. The web was then transferred to a transfer fabric (Lindsay Wire 952-505) using a vacuum shoe at a first transfer point with no significant speed differential between the two fabrics. The web was further transferred from the transfer fabric to a woven through-drying fabric at a second transfer point using a second vacuum shoe. The through drying fabric used was a Lindsay Wire T-116-3 design (Lindsay Wire Division, Appleton Mills, Appleton, Wis.), based on the teachings of U.S. Pat. No. 5,429,686 issued to Kai F. Chiu et al. The T-116-3 fabric is well suited for creating molded, three-dimensional structures. At the second transfer point, the through-drying fabric was traveling more slowly than the transfer fabric, with a velocity differential of 2.8%. The web was then passed over a hooded through-dryer where the sheet was dried. The hood temperature was approximately 200° F. The dried sheet was then transferred from the through-drying fabric to another fabric, from which the sheet was reeled. The pilot paper machine for producing the uncreped paper was operated at a speed of approximately 20 feet per minute. The basis weight of the dry basesheet was approximately 39 gsm (grams per square meter). The sheet had a thickness of 0.64 mm when measured with a platen gauge at 0.05 psi, for a dry bulk of 16.4 cc/g. The Surface Depth is about 0.42 mm.

Samples of the basesheet were conditioned under Tappi environmental conditions for several days, then cut to a number of 6 in×12 in sheets which were then treated with paraffin wax using a variety of methods. A rectangular slab of Gulfwax™ paraffin for home canning was used to apply a small quantity of wax on the fabric side surface of the uncreped basesheet produced as described above. Several basesheet samples were heated individually on a Corning PC-351 hot plate set at a low power level of 2.5. The samples were held in light contact with the heated surface by hand for 5 to 10 seconds, then removed and placed on a table. The slab of wax was them immediately dragged over the heated sample surface to deposit a small quantity of wax on the most elevated regions of the upper surface. In one version, the fabric side of the basesheet was in contact with the heated surface, while in a second version, the air side of the basesheet was heated. In applying the wax, the slab was held at about a 300 angle relative to the plane and the lower end of the slab was placed on the basesheet. The slab was then dragged with light force (estimated at about 0.5 to 1 pound) over one entire surface of the basesheet such that the contacting end of the slab was the trailing edge. Care was taken to apply the wax uniformly. The objective was to avoid melting the wax since the melted wax would impregnate the basesheet and not remain on the surface, but to facilitate the deposition of wax onto the basesheet through heat. Heating and wax treatment was done successively on sections about 3-inches square or 6-inches square until the entire basesheet sample was treated. The wax slab was weighed before and after application. The typical amount of wax applied to the 6 in×12 in basesheet was about 0.06 g.

Upon subsequent wetting of the resulting absorbent web, minute upper sections of the wax-treated web appeared slightly lighter than untreated regions, as if the wax had trapped some air next to the fibers. Based on the physical appearance, it was evident that wax was preferentially distributed on the uppermost regions of the basesheet surface, occupying a small fraction of the total surface area estimated to be about 10%.

Figure 15:
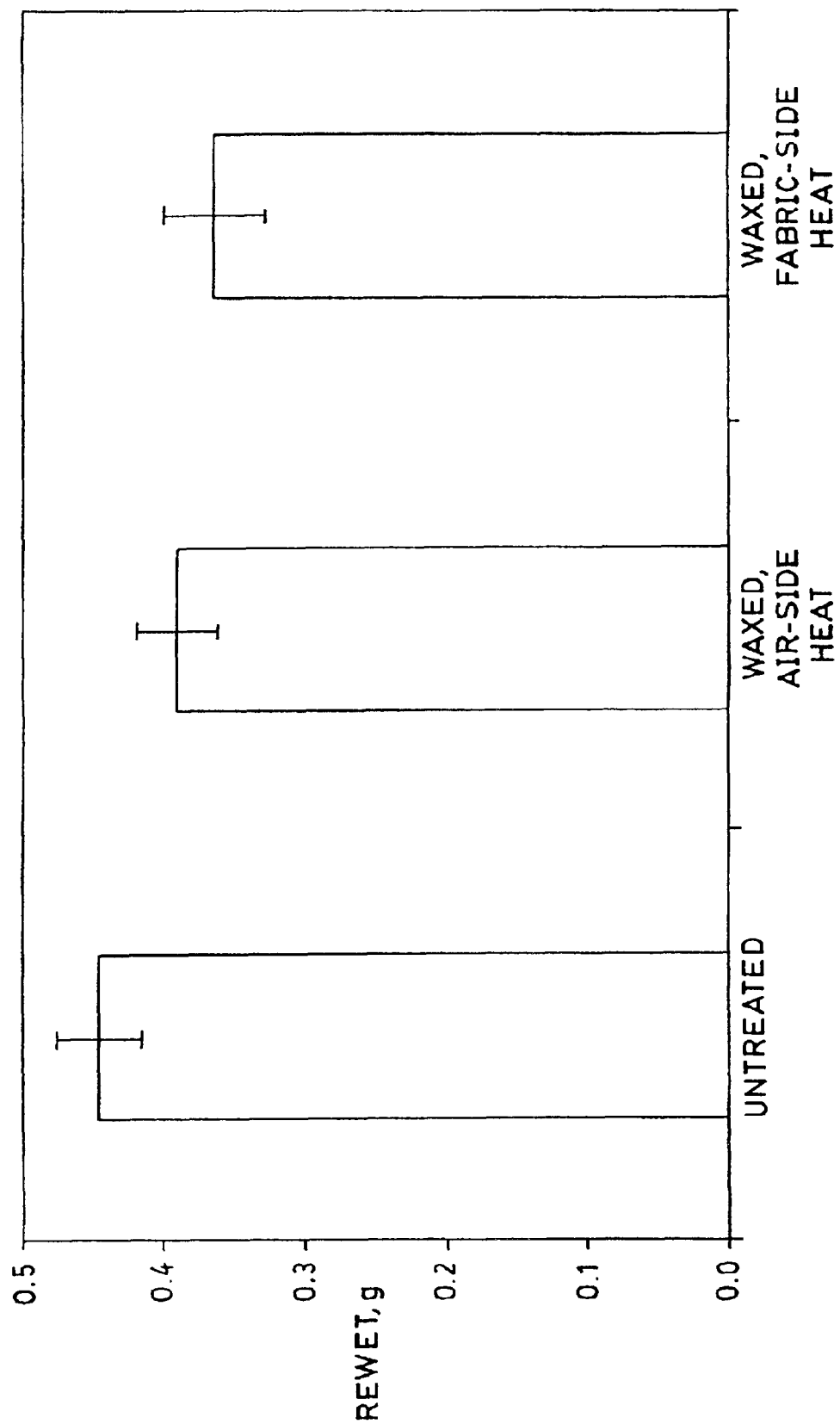
FIG. 15 is a graph of mean Rewet values and 95% confidence intervals for samples of Example 1.

Mean Rewet values for untreated and wax-treated samples are shown in Table 1. Also listed are mean Normalized Rewet values (Rewet divided by the conditioned dry mass of the sample). The graph in FIG. 15 depicts the mean values and the 95% confidence intervals about the means (1.96* standard deviation/square root of sample size). The treatment with paraffin resulted in a significant decrease in Rewet. The decrease in Rewet value is assumed to be indicative of a dryer feel if the tissue were wetted in contact with skin, for less fluid could pass through the local, elevated hydrophobic barriers to contact the skin. The wax-treated samples also felt slightly less gritty than the untreated samples, apparently due to some degree of lubricity afforded by the paraffin on the highest portions of the treated surface.

TABLE 1

Rewet Values for Example 1

| Treatment Method | Rewet Value, g | Normalized Rewet (Rewet/Dry Mass) |
| --- | --- | --- |
| Untreated | 0.446 | 0.706 |
| Wax, air-side heat | 0.390 | 0.629 |
| Wax, fabric-side heat | 0.363 | 0.564 |

Example 2

In order to further illustrate this invention, uncreped throughdried tissue basesheet was produced using the method substantially as described in Example 1. More specifically, single-layer, single-ply tissue was made from unrefined northern softwood bleached chemithermomechanical pulp (BCTMP) fibers. After pulping and dilution of the BCTMP fibers, Kymene 557LX was added at 20 kilograms per metric ton of pulp. The forming fabric in this case was an Appleton Wire 94M fabric and the first transfer fabric was a Lindsay 956 fabric. Rush transfer was performed at the first transfer point, during the transfer from the forming fabric to the Lindsay 956 transfer fabric. The degree of rush transfer was 35%. The differential velocity transfer process used the vacuum shoe geometry taught in U.S. Pat. No. 5,667,636, issued Mar. 4, 1997 to S. A. Engel et al., previously incorporated by reference. At this second transfer point, from the transfer fabric to the through-air drying, both fabrics were running at substantially the same speed of about 40 feet per minute. The web was then transferred to a throughdrying fabric (Lindsay Wire T116-3). The throughdrying fabric was traveling at a speed substantially the same as the transfer fabric. The web was then carried over a throughdryer operating at a hood temperature of about 315° F. and dried to final dryness of about 94–98 percent consistency. The basis weight of the web was 60 gsm.

The resulting uncreped throughdried tissue basesheet was used in measurements of In-Plane Permeability using a stack of two disks, yielding a value of $1.87 \times 10^{-10}$ $m^2$. Wet resiliency testing gave a WCB (Wet Compressed Bulk) value of 9.65 cc/g, a Springback of 0.889, and an LER of 0.824. The bulk measured at 0.1 psi was 16.2 cc/g.

After several weeks of storage under Tappi environmental conditions, the basesheet was then treated with paraffin wax essentially as described in Example 1. Two strips were prepared, 12 inches×6 inches. For each strip, the fabric side of a 6-inch square region was heated in contact with the Corning PC-351 hot plate at a power setting of 2.5 for about 5 seconds, then removed and placed fabric-side up on a flat surface. A slab of paraffin wax was then dragged over the surface to deposit about 0.06 g of wax on the surface of the first strip and 0.07 g of wax on the surface of the second. The two strips were then cut into 4-inch×6-inch segments. All segments from the first strip (labeled 1A, 1B, and 1C) were tested for Rewet and one segment from the second strip was tested in addition to 3 similar untreated strips of the same basesheet (labeled 3, 4, and 5). Results are shown in Table 2. Rewet values for the waxed segments were significantly lower than the untreated samples, with the exception of segment 1A, which had a value similar to untreated samples. This sample was excessively wet, beyond the recommended range for the test, so the additional available moisture may have inflated the Rewet value. However, it is suspected that the waxing operation may have been performed poorly in the region that would later be in contact with the Whatman filter paper during testing. The mean Rewet for the waxed samples, excluding sample 1A, is 0.467 g compared to the untreated mean of 0.689 g, an apparent reduction of 32%. Normalized Rewet also drops significantly due to hydrophilic treatment. Here, Rewet values less than 0.68 g are taken as evidence of improved dry feel.

TABLE 2

Rewet Values for Example 2

| Sample | Treatment | Dry Mass | Wet Mass | Rewet, g | Normalized Rewet (Rewet/Dry Mass) |
| --- | --- | --- | --- | --- | --- |
| 1A | Waxed | 0.93 | 3.95 | 0.628 | 0.675 |
| 1B | Waxed | 0.94 | 3.82 | 0.438 | 0.466 |
| 1C | Waxed | 0.98 | 4.06 | 0.525 | 0.536 |
| 2 | Waxed | 1.01 | 4.14 | 0.437 | 0.433 |
| 3 | Unwaxed | 0.97 | 3.98 | 0.680 | 0.701 |
| 4 | Unwaxed | 1.00 | 4.06 | 0.692 | 0.692 |
| 5 | Unwaxed | 1.03 | 4.26 | 0.695 | 0.675 |

To determine if the small amount of presumably dominantly surface wax applied to the textured basesheets had any adverse effect on total absorbent capacity, the tested segments were fully immersed in tap water and then held by a corner and allowed to drip for 60 seconds, then weighed. The "Dripping Wet Mass" for untreated samples 3 and 5 was 7.8 and 8.3 g, respectively. The "Dripping Wet Mass" for samples 1A, 1B, and 1C was 7.44, 7.55, and 7.9 g, respectively. For sample 2, it was 8.00 g. Given the variability and overlap of the data ranges for treated and untreated samples, there is no clear evidence of a significant decrease in absorbent capacity of the waxed samples.

Examples 3–6

In order to further illustrate a method of making absorbent webs of this invention, basesheets were produced using non-wet resilient northern softwood kraft fibers (NSWK), with and without a wet strength agent (20 lbs Kymene/ton of fiber), and wet resilient fibers (spruce BCTMP), with and without a wet strength agent (20 lbs Kymene/ton of fiber), using an uncreped throughdried process substantially as shown in FIG. 4.

The fiber was pulped at 4% consistency in the hydropulper for 30 minutes. The fiber was pumped into a stock chest and diluted to 1.0% consistency. 20#/ton of Kymene 557 LX was added to the stock chest and allowed to mix for 30 minutes. A single-layer, blended sheet of 30 gsm dry weight was formed on an Albany 94M forming fabric and dewatered with 5 inches (127 millimeters) of mercury vacuum. The forming fabric was traveling at 69 fpm (0.35 meters per second). The sheet was transferred at a 15% rush transfer to a Lindsay 952-S05 transfer fabric traveling at 60 fpm (0.30 meters per second). The vacuum in the transfer between the forming fabric and transfer fabric was 10 inches (254 millimeters) of mercury.

The sheet was vacuum transferred at 12 inches (305 millimeters) of mercury to a throughdryer fabric (Lindsay T116-1) traveling at the same speed as the transfer fabric, 60 fpm (0.30 meters per second). The sheet and throughdryer fabric traveled over a fourth vacuum at 12 inches (305 millimeters) of mercury just prior to entering a Honeycomb throughdryer operating at 200° F. (93° C.) and dried to a final dryness of 94–98% consistency.

The basesheets were aged for over 5 days at less than 50% humidity at 70° F. (21° C.). The basesheets were tested for physical characteristics in a controlled environment of 50%±2% humidity and 23° C.±1°. The wet and dry strength were Instron tested with a 3-inch (7.62 cm) sample width, 4-inch (10.16 cm) jaw span at 10 in/min (25.4 cm/min) crosshead speed. Caliper was measured with the TMI tester at 0.289 psi.

Physical property results are shown in the table of FIG. 16. Example 6 exhibited substantially greater wet resiliency, as measured by the Wet Wrinkle Recovery Test, than the other three samples. In addition, Example 6 also showed a high wet:dry ratio. The properties of Example 6 in particular make it suitable for use as a basesheet that can be calendered and later recover much of its original bulk upon wetting. When treated with hydrophobic materials such as silicones or talcum powder, such a calendered absorbent web can provide high absorbency and a dry feel when the hydrophilic regions rise from the remainder of the sheet after wetting.

Examples 7–10

Further examples were carried out similar to those described in Examples 3–6, but for the purpose of exploring the basis weight effect on a bulky, absorbent, wet resilient structure. Four basis weight levels of 30, 24, 18 and 13 gsm of 100% Spruce BCTMP with 20#/ton Kymene were produced.

The fiber was pulped at 4% consistency in the hydropulper for 30 minutes. The fiber was pumped into a stock chest and diluted to 1.0% consistency. 20#/ton of Kymene 557 LX was added to the stock chest and allowed to mix for 30 minutes. A single-layer, blended sheet was formed on an Albany 94M forming fabric and dewatered with 4 inches (102 millimeters) of mercury vacuum. The forming fabric was traveling at 69 fpm (0.35 meters per second). The sheet was transferred at a 15% rush transfer to a Lindsay 952-S05 transfer fabric traveling at 60 fpm (0.30 meters per second). The vacuum in the transfer between the forming fabric and transfer fabric was 7 inches (178 millimeters) of mercury. The 13 gsm sample was produced without a rush transfer, the forming fabric was traveling at 60 fpm (0.30 meters per second), the same as the transfer fabric and throughdryer fabric.

The sheet was vacuum transferred at 10 inches (254 millimeters) of mercury to a throughdryer fabric (Lindsay T116-1) traveling at the same speed as the transfer fabric, 60 fpm (0.30 meters per second). The sheet and throughdryer fabric traveled over a fourth vacuum at 11 inches (279 millimeters) of mercury just prior to entering a Honeycomb throughdryer operating at 260° F. (127° C.) and dried to a final dryness of 94–98% consistency.

The basesheets were aged for over 5 days at less than 50% humidity at 70° F. (21° C.). The basesheets were tested for physical characteristics in a controlled environment of 50%±2% humidity and 23° C.±1°. The wet and dry strength were Instron tested with a 3-inch (7.62 cm) sample width, 4 inch (10.16 cm) jaw span at 10 in/min (25.4 cm/min) crosshead speed. The caliper was measured with the TMI tester at 0.289 psi.

Physical property results are summarized in the table of FIG. 17. As shown, examples 7–10 exhibited high wet resiliency as determined by the Wet Wrinkle Recovery Test and the Compressive Wet Resiliency tests. Materials such as the web of Example 10 are especially suitable as a basesheet to receive hydrophobic matter in the production of a dense, calendered absorbent web that can rapidly absorb liquid and then spring back to a bulkier structure having hydrophilic material on the uppermost regions to provide a clean, dry feel. Typical commercial tissue and paper towels generally have Wet Springback Ratios of less than 0.7, WCB values less than 6, and LER values less than 0.7. Likewise, such materials tend to have In-plane Permeability values below $0.4 \times 10^{-10}$ m$^2$.

Examples 11 and 12

For Examples 11 and 12, the fabric side of the basesheet of Example 1 was treated with adhesive sprays to create scattered hydrophobic regions, some of which were further treated with hydrophobic powder. For Example 11, a spray can of 3M #72 Pressure Sensitive Adhesive was used to randomly cover about 30% of the surface area of the basesheet with the blue, flexible, soft, and low-tack adhesive material. Tack was further reduced by sprinkling a small quantity of lycopodium powder (also known as club moss spores, commercially available from EM Science, Gibbstown, N.J.) on one portion of the web and talc powder on another portion to selectively adhere to the adhesive and remove the tacky sensation. Unattached powder was shaken off. For Example 12, the spray adhesive used was 3M #90 High Strength Adhesive, which was randomly and lightly sprayed to yield scattered patches about ½ to 1 inch in diameter containing adhesive on the upper surface. Tack was again reduced by sprinkling talk or lycopodium powder on various portions of the web and removing excess powder. When the webs were wetted, the hydrophobic regions containing adhesive and hydrophobic powder felt somewhat drier than the untreated regions. The adhesive-containing regions of Example 12 were noticeably stiffer than the surrounding basesheet and would be unsuitable for many products. The lower viscosity of the adhesive used in Example 12 also resulted in relatively more penetration of the adhesive into the absorbent web relative to Example 11, so the adhesive patches of Example 12 appeared lighter than the surrounding untreated regions when the absorbent web was fully wetted with water.

Example 13

Additional uncreped, through-air dried basesheets were made according to Example 2. Example 13 differed in having 10 pounds of Kymene per ton of dry fiber in the furnish, had 15% rush transfer, and comprised 75% northern softwood kraft fibers and 25% spruce BCTMP. As with Example 2, the basis weight was 60 gsm and the through-air drying fabric was a Lindsay Wire T116-3 fabric. The measured Wet Springback Ratio was 0.839, WCB was 7.5 cc/g, and LER was 0.718. In-plane Permeability was $0.84 \times 10^{-10}$ m$^2$.

The basesheet of Example 13 could be made into a web of the present invention by blade coating the upper surfaces of the fabric side of the basesheet with a flexible, hydrophobic, low-tack hot melt adhesive at elevated temperature immediately followed by air laying fine synthetic fibers having an average length of about 1 mm on the adhesive-containing side of the web, followed by light air jets to blow off and recover unattached fibers. Cooling jets may be desired to remove tack of the adhesive before reeling. Tack reduction of exposed adhesive may also be accomplished by the addition of particulates entrained in air jets applied to the treated web, said particulates comprising talc, baking soda, titanium oxide, zinc oxide, miscellaneous fillers known in papermaking, and the like.

The foregoing examples serve to illustrate possible approaches pertaining to the present invention in which improved dry feel and other properties are achieved through novel combinations of resilient, textured basesheets with hydrophobic matter. However, it will be appreciated that the foregoing examples, given for purposes of illustration, are not to be considered as limiting the scope of this invention which is defined by the following claims and all equivalents thereto.

Example 14

A 0.6 osy polyethylene spunbond nonwoven web was laminated with construction adhesive to the fabric side of a 40 gsm uncreped, through-air dried web comprising 100% BCTMP spruce fibers and textured by through drying on a Lindsay Wire T-216-3 fabric. A strip of airlaid cellulosic web was prepared that had been densified and stabilized with about 1% thermoplastic fibers which melted during heating to hold the strip at a constant density of about 0.2 g/cc. The 1-inch wide strip was placed underneath the uncreped basesheet with the attached nonwoven web on top. Fluid intake was tested by placing drops of dyed water on the upper surface. The water rapidly penetrated into the tissue basesheet and then into the airlaid strip, resulting in the majority of the fluid being held by the airlaid material. When colored drops of water were placed on the laminated web without an underlying airlaid absorbent, the fluid spread over a much greater area in the basesheet than when the airlaid strip was present.

A mixture of about equal parts egg white and water, with some green commercial food coloring added, was prepared to simulate the intake of viscoelastic fluids such as mucous or menses. The solution was gently stirred to establish a uniform consistency. The solution was then applied as drops of about 0.3 ml to about 1 ml to the surface of the intake material with the airlaid strip underneath. Intake seemed very slow or even completely impeded by the nonwoven material. The tip of a knife blade was then used to scratch away a small portion of the nonwoven web, resulting in an aperture about 0.2 mm wide and 2 mm long. A drop of the egg white solution applied to the aperture penetrated into the hydrophilic within a few seconds, much more rapidly than without the aperture, yet still more slowly than the less viscous and non-viscoelastic colored water.

Example 15

To demonstrate the potential of apertured nonwoven fabrics in the present invention, three polyethylene non-woven spunbond webs were acquired having basis weights of 0.4, 0.6, and 0.8 ounces per square yard (osy). The webs were apertured using a roll device for twin aperturing. Metallic pins were mounted in holes in curved metal plates that could be bolted onto the midsection of an upper roll. Matching metal plates with holes mounted to the lower roll received the upper tapered portion of the pins in the upper roll. Two different pin diameters were used, 0.109-inches and 0.187-inches. The holes for receiving and holding pins were arrayed in a bilaterally staggered grid. The 0.187-inch pins were placed into every hole in the array over a two-inch wide strip around the upper roll. Roll perimeter is 36 inches. The 0.187-inch pins were thus spaced apart at about 0.25-inch intervals from center to center along any row. The 0.109-inch pins were spaced apart over a 4-inch wide strip of bilaterally staggered holes, with pins loaded only in alternating rows and in any row containing pins, loaded only into every other hole of that row. With 11 pins in each 4-inch wide row, the loaded 0.109-inch pins are spaced apart by about 0.4-inches from center to center. To improve the quality of the aperturing, the upper roll containing the pins is heated to about 200° F. and the lower roll, which contacts the nonwoven web, is electrically heated to 150° F. These are temperatures measured inside the roll. Using a surface thermocouple, the upper surface temperature of the upper roll was measured at 150–158° F. Using the 0.109-inch pins first, the aperturing device was driven at 50 fpm and used to aperture lengths of polyethylene spunbond material having a basis weight of 0.4, 0.6, and 0.8 osy (ounce per square yard). Then the plates containing pins were switched to permit aperturing with the 0.187-inch diameter pins, also at 50 fpm and all three spunbond basis weight materials were apertured. The apertured nonwoven web appeared soft and suitable for use as a feminine care material. Samples of the nonwoven webs were then cut and placed on sections of uncreped, through-dried material made according to Wendt et al., previously incorporated by reference, and textured on three-dimensional through drying fabric from Lindsay Wire according to Wendt et al. and Chiu et al., also previously incorporated by reference.

Though 3M pressure sensitive spray adhesive was used at one point to join the tissue basesheet and the nonwoven web, joining the apertured nonwoven to the textured uncreped tissue web was simplified by a natural mechanical affinity of the tissue surface for the loopy nonwoven surface. Engagement of fibrils apparently allows the nonwoven layer to adhere reasonably well, though it is preferred to create a more intimately bonded structure through any of adhesive bonding, ultrasonic bonding, thermal bonding, and the like.

Example 16

Composite topsheet structures were prepared by adhering the apertured webs of Example 15 to textured, uncreped, through air dried basesheets, similar to those described in Examples 1–10. Adhesion was achieved with a specialty adhesive transfer paper comprising a coated release paper printed with dots of adhesive, such that the dots could be transferred to other surfaces by mild application of pressure. A hot melt construction adhesive was used, National Starch #5610, printed on a coated release paper via screen printing with a New England Rotary screen, 40-NERO-SF0001. To join an apertured nonwoven web to the textured tissue paper, the adhesive transfer paper was placed with the adhesive dots in contact with textured tissue and then pressed lightly with a rubber roller at a load of less than 0.5 pounds per linear inch such that the web was not substantially flattened by the roller and such that a portion of the adhesive dots transferred to the most elevated portions of the web. The apertured nonwoven web was then superposed on the tissue. In placing the nonwoven web on the tissue web, the side of the nonwoven web that contacted the tissue was the side which was away from the roll holding the pins during the pin aperturing process. This tissue-facing side of the nonwoven web had protrusions surrounding each aperture where the pin had forced some of the polyolefin material out of the plane of the nonwoven web during the pin aperturing process. In some cases, it may be preferably that such protrusions should reside primarily in depressed regions of the underlying tissue web to provide a nearly continuous material bridge from the body-facing side of the nonwoven web to the tissue surface, such that fluid does not need to cross any significant interfacial gaps between the two or more layers of the topsheet.

For these examples, only 0.4 osy basesheet nonwoven spunbond webs were used. The basesheets were all unlayered, uncreped, through-air dried tissue webs made according to the principles given in Examples 1–10, with the exception that basis weight, fiber type, rush transfer, and fabric types were varied. "High texture" refers to webs made with about 30% rush transfer onto a Lindsay Wire T-116-3 fabric as the transfer fabric, followed by through drying on a T-216-3 fabric. "Flat" tissue was through dried on a traditional flat through drying fabric lacking high surface depth. "Medium texture" refers to webs made with 8% rush transfer onto a Lindsay Wire T-216-3 fabric as the transfer fabric, followed by through drying on a Lindsay Wire T-116-3 fabric. All webs had about 20 lb Kymene per ton of fiber added for wet strength. The following combinations of nonwoven and basesheet were tested:

TABLE 3

Composites tested for intake.

| Sample | Aperturing | Basesheet |
|---|---|---|
| 1 | none | 30 gsm, 100% BCTMP, high texture |
| 2 | 0.109" pins | 30 gsm, 100% BCTMP, high texture |
| 3 | 0.187" pins | 30 gsm, 100% BCTMP, high texture |
| 4 | 0.187" pins | 30 gsm, 100% BCTMP, flat |
| 5 | 0.187" pins | 30 gsm, 100% BCTMP, high texture |
| 6 | 0.187" pins | 50 gsm, 50% bleached northern softwood, 50% mercerized bleached southern softwood, medium texture |
| 7 | 0.187" pins | 30 gsm, 100% BCTMP, flat |

In some cases, the cover material was combined with a thin absorbent layer consisting of another uncreped, through-air dried sheet or an air-laid strip. These absorbent layers include:

Abs. A: a "high texture" 100% BCTMP web (Sample 1 of Table 3)

Abs. B: a "flat" 100% BCTMP web (Sample 4 of Table 3);

Abs. C: a 100% BCTMP uncreped web through-dried on a Lindsay Wire 134-10 fabric;

Abs. D: a "medium texture" web comprising bleached softwood (Sample 6 of Table 3)

In addition, the airlaid strip of Example 14, having a basis weight of about 200 gsm, was also used in some tests. The absorbent layer was simply placed beneath the composite cover and was not joined mechanically or with adhesives. In some cases, light adhesive might be desirable to hold the cover onto the absorbent core.

To demonstrate the suitability of the apertured webs of Example 15 for intake of menses, a simple menses simulant was used. The simulant was a 50:50 mixture of fresh egg whites and water, with added fugitive dye. The mixture was prepared by separating the egg whites from the yolks for two large eggs (Sparboe Farms, Litchfield, Minn.) that had been removed from refrigeration and placed in a room with a temperature of approximately 72° F. for six hours. The egg white mass was 60.0 g. An additional 60 g of deionized water was added to the egg whites in a 250 ml beaker and stirred vigorously in the beaker with a laboratory spatula for about 3 minutes, taking care to prevent froth formation. The resulting mixture appeared slightly turbid and still showed signs of proteinaceous strands in the fluid having a different refractive index that other parts of the solution. An additional 2 ml of a dye solution was stirred in gently. The dye solution was prepared by adding 40 ml of Versatint Purple II due (Milliken Chemical, Inman, S.C.) to 1000 ml of deionized water.

The colored egg white solution was applied to the surface of the composite topsheet material with an Eppendorf pipette set to apply 0.5 ml droplets. The droplet was applied to the upper surface of the topsheet within a 3 second interval, taking care to apply the drop gently and smoothly. Initially the drop balled up, resting on the nonwetting surface as a flattened sphere several millimeters in diameter, broad enough to engage at least one aperture, typically regardless of where the drop was placed. Then visual observation was used to identify the time required for wicking to occur in the plane of the underlying basesheet, and the additional time after the onset of wicking for the drop to be substantially removed from the surface of the nonwoven web, such that essentially no remaining liquid remained noticeably elevated above the plane of the nonwoven web. The first time, the time for visible wicking to begin, is termed the "entry time," and was detected when colored fluid could be seen extending horizontally in the basesheet beyond the margins of the drop on top. The second time, the time for substantial removal of the liquid from drop on the nonwoven surface is the "wicking time." The sum of the two times is the "intake time." Results are shown for several trials in Table 4. Best results were obtained with the larger pin apertures. With the smaller apertures, the hydrophobic fibers in the protrusion on the back side of the web formed during aperturing may have become flattened to partially close off apertures during attachment to the uncreped tissue web.

TABLE 4

Intake results for egg-white solutions for the composites of Table 3.

| Run | Sample | Entry time (s) | Wicking time (s) | Intake time (s) |
|---|---|---|---|---|
| 1 | 1 | >500 | NA | >500 |
| 2 | 2 | >500 | NA | >500 |
| 3 | 3 | 70 | 90 | 160 |
| 4 | 3 + Abs. A | 20 | 80 | 100 |
| 5 | 4 + Abs. B | 10 | 50 | 60 |
| 6 | 4 + Abs. B | 0 | 25 | 25 |
| 7 | 5 + Abs. C | 10 | 30 | 40 |
| 8 | 5 + Abs. C | 0 | 40 | 40 |
| 9 | 6 + Abs. D | 5 | 35 | 40 |
| 10 | 7 | about 200 | about 200 | about 400 |
| 11 | 4 + air laid | 10 | 150 | 160 |
| 12 | 4 + air laid | >500 | NA | >500 |
| 13 | 5 + Abs. C | 10 | 70 | 80 |
| 14 | 6 + air laid | 5 | 200 | 205 |
| 15 | 6 + air laid | >500 | NA | >500 |

It is believed that intake rates could be increased significantly by increasing the exposed area of the basesheet.

By placing drops of the egg white solution directly on BCTMP and bleached softwood uncreped sheets, it was observed that BCTMP offers more rapid intake, apparently because of the more open pore structure of the BCTMP sheet. Densified air laid strips with a density of about 0.2 cc/g also gave rapid intake of the solution.

Example 17

The ability of the present invention to serve as an improvement over apertured films can be envisioned in this example, wherein a moist hydrophilic basesheet is provided with a non-planar apertured structure and then noncompressively dried to impart high wet resiliency, followed by printing or coating of hydrophobic matter on the most elevated regions of the body-contacting side of the apertured web, resulting in a composite material having hydrophilic apertures and a hydrophobic upper surface. In particular, a soft, flexible web of basis weight from about 10 gsm to about 100 gsm, more preferably from about 20 gsm to about 50 gsm, during manufacture is apertured before the web has dried to above about 60% solids, and preferably before the web has dried above about 40% solids. The web may be relatively flat or textured prior to aperturing. Aperturing can be done by protrusions on a roll contacting the body side of the web while residing on a surface having mating depressions, such that intermeshing of the protrusions and the depressions causes apertures to descend away from the body-contacting side of the web to create a non-planar, three-dimensional topography with regions of the web adjacent the apertures having some z-direction fiber orientation. Apertures in the basesheet can also be created by needling, perf-embossing, stamping, or differential air pressure. Differential air pressure can be used when the web resides on a perforated but otherwise low-permeability carrier. The weak, moist web residing on a perforated surface permits air pressure to cause portions of fibers over the perforations to deflect and break free from the plane of the web and to descend partly in the z-direction. After the 3-D apertures are created in the moist state, the web should be dried to completion without significantly disrupting the perforated or apertured state it has achieved. The structure of the web will then have high wet resiliency, particularly if low yield fibers or wet strength additives are used. As a result, the basesheet is provided with apertures and the lower surface of the basesheet is provided with fibrous protrusions descending from the basesheet which are adjacent to the apertures and may surround or partially surround the apertures, forming hydrophilic aperture walls. The protrusions or aperture walls, by virtue of being dried in their three-dimensional state, also have good wet resiliency, or a tendency to maintain the form and orientation in which they were dried even after being wetted, especially if high yield fibers or wet strength agents were used in making the web. Preferably, the apertures have an open area of at least 15% and more preferably at least 30%, and have a characteristic or effective diameter preferably of from about 0.2 mm to about 4 mm, more specifically from about 0.3 mm to about 2 mm, and most specifically about 0.5 mm or greater.

After non-compressive drying, the body-contacting side of the web (the side remote from the descending sides of the apertures) is treated with hydrophobic matter. This may be printed onto the web in discontiguous drops or fine spaced apart regions. Alternatively, the web may be coated or printed by a smooth printing surface having a film of the hydrophobic matter in the molten, liquid state, or slurry state. Waxes or mixtures of wax, oil, and opacifiers may be especially preferred. The resulting structure has hydrophobic elevated regions while the walls of the apertures descending away from the hydrophobic matter are still hydrophobic. The hydrophobic matter is intimately bonded to the surface of the hydrophilic web. Because the basesheet is providing structural integrity, the hydrophobic matter can be continues but weak or discontiguous, and generally would not be expected to be capable of being removed from the basesheet without being severely damaged or disintegrating. It provides a dry feel adjacent the body and, if properly selected, can enhance the soft, pleasant feel of the cover. The underlying basesheet provides excellent absorbency and provides conduits like traditional apertured films for flow direct to the absorbent core. However, in-plane wicking and flow channels underneath the basesheet will provide for good fluid handling and absorbent capacity.

It will be appreciated that the foregoing examples, given for purposes of illustration, are not to be construed as limiting the scope of this invention, which is defined by the following claims and all equivalents thereto.

We claim:

1. A method for producing an absorbent article comprising the steps of:
    a) preparing a wet resilient, cellulosic basesheet having elevated and depressed regions with an Overall Surface Depth of at least 0.2 mm. and having an upper surface and a lower surface;
    b) integrally attaching a contiguous, fibrous nonwoven web having a plurality of openings onto the upper surface of the cellulosic basesheet such that a portion of the openings are superposed over the depressed regions of the cellulosic basesheet;
    c) attaching the lower surface of the basesheet to an absorbent core and an impervious web, such that the absorbent core is sandwiched between the impervious web and the basesheet.
2. The method of claim 1 wherein said basesheet is a wet-laid tissue sheet.
3. The method of claim 1 wherein said basesheet is an airlaid structure.
4. The method of claims 1 wherein the basesheet is further characterized by a Wet Springback Ratio of about 0.7 or greater.
5. The method of claim 1 wherein the basesheet is further characterized by a Rewet value of about 0.65 g or less and a Normalized Rewet value of about 0.6 or less.
6. The method of claim 1 wherein said basesheet has an In-Plane Permeability of at least $0.5 \times 10-10$ m$^2$, and a Wet Compressed Bulk of about 5 cc/g or greater.
7. The method of claim 1 further comprising hydrophobic matter on a portion of the lower surface of said basesheet.
8. The method of claim 1 wherein said basesheet has an Overall Surface Death of about 0.2 mm or less while dry and an Overall Surface Depth of about 0.3 mm or areater when wetted to a moisture content of 100%.
9. The method of claim 1 wherein said basesheet has a wet:dry tensile ratio of at least 0.1.
10. The method of claim 1 wherein said elevated regions comprise from 5 to 300 protrusions per square inch having a characteristic height of at least 0.2 mm relative to said depressed regions.
11. The method of claim 1 further comprising superabsorbent particles attached to said basesheet.
12. The method of claim 1 wherein said basesheet is further characterized by a wet:dry tensile strength ratio of at least about 0.1 or greater and a Wet Springback Ratio of about 0.55 or greater.
13. The method of claim 1 wherein the basesheet is further characterized by a Rewet value of about 0.65 g or less and a Normalized Rewet value of about 0.6 or less, said basesheet further comprising about 20% or greater by weight high yield pulp fibers.
14. The method of claim 1 wherein said basesheet further comprises apertures and said lower surface of the basesheet further comprises wet-resilient protrusions adjacent said aperture.
15. A method for producing an intake material for an absorbent article, comprising the steps of
    a) forming an embryonic paper web from an aqueous slurry of papermaking fibers;
    b) through-drying the embryonic paper web on a three-dimensional through-drying fabric having a pattern of elevated and depressed regions;
    c) completing the drying of the web;
    d) aperturing a nonwoven web by means of hydroentangling, wherein the nonwoven web overlays a carner fabric having substantially the same pattern of elevated and depressed regions as the through-drying fabric of step (b);
    e) joining the apertured nonwoven web with the through-dried paper web such that the apertures of the nonwoven web are substantially aligned with the depressed regions of the through-dried paper web.

* * * * *